United States Patent
Berkman et al.

(10) Patent No.: US 11,147,889 B2
(45) Date of Patent: Oct. 19, 2021

(54) ALBUMIN-BINDING PSMA INHIBITORS

(71) Applicant: Cancer Targeted Technology LLC, Woodinville, WA (US)

(72) Inventors: Clifford Berkman, Pullman, WA (US); Cindy Choy, Pullman, WA (US)

(73) Assignee: Cancer Targeted Technology LLC, Woodinville, WA (US)

( * ) Notice: Subject to any disclaimer, the term of this patent is extended or adjusted under 35 U.S.C. 154(b) by 0 days.

(21) Appl. No.: 16/349,756

(22) PCT Filed: Nov. 24, 2017

(86) PCT No.: PCT/US2017/063182
§ 371 (c)(1),
(2) Date: May 14, 2019

(87) PCT Pub. No.: WO2018/098390
PCT Pub. Date: May 31, 2018

(65) Prior Publication Data
US 2020/0061218 A1    Feb. 27, 2020

Related U.S. Application Data

(60) Provisional application No. 62/425,810, filed on Nov. 23, 2016.

(51) Int. Cl.
*A61K 49/10*    (2006.01)
*C07D 225/08*    (2006.01)

(52) U.S. Cl.
CPC .......... *A61K 49/106* (2013.01); *C07D 225/08* (2013.01)

(58) Field of Classification Search
CPC .............. A61K 51/081; A61K 51/0402; A61K 49/106; A61P 35/00; A61P 13/08; Y02P 20/55; C07D 225/08
See application file for complete search history.

(56) References Cited

U.S. PATENT DOCUMENTS

| | | | |
|---|---|---|---|
| 2010/0172844 A1* | 7/2010 | Neri | A61P 35/00 424/9.365 |
| 2013/0034494 A1 | 2/2013 | Babich et al. | |
| 2017/0267717 A1* | 9/2017 | Neumaier | C07B 59/002 |
| 2017/0368005 A1* | 12/2017 | Babich | A61K 51/0402 |
| 2018/0194729 A1* | 7/2018 | Cardinale | G01N 33/57434 |
| 2020/0155713 A1* | 5/2020 | Ray | C07B 59/004 |

FOREIGN PATENT DOCUMENTS

| WO | 2013/028664 | 2/2013 |
|---|---|---|
| WO | 2015/069932 | 5/2015 |
| WO | 2015/073678 | 5/2015 |

OTHER PUBLICATIONS

Cann, Biophysical Journal, 1961, 1, p. 711-21. (Year: 1961).*
Shallal et al., "Heterobivalent Agents Targeting PSMA na Integrin-[alpha] v 3", Bioconjugate Chemistry, vol. 25, No. 2, Feb. 19, 2014, pp. 393-405.
International Search Report dated Feb. 5, 2018 for International Application No. PCT/US2017/063182 filed Nov. 24, 2017, 4 pages.

* cited by examiner

*Primary Examiner* — Michael G. Hartley
*Assistant Examiner* — Leah H Schlientz
(74) *Attorney, Agent, or Firm* — McDonnell Boehnen Hulbert & Berghoff, LLP

(57) ABSTRACT

Provided herein are compounds of Formula (I) or a pharmaceutically acceptable salt thereof, wherein $L^1$ and $L^2$ are each independently a covalent bond or a divalent linking group, R is a detectable label or therapeutic drug and B is an albumin binding moiety. Also provided are compositions including a compound of Formula (I) together with a pharmaceutically acceptable carrier, and methods for imaging prostate cancer cells using a compound of Formula (I).

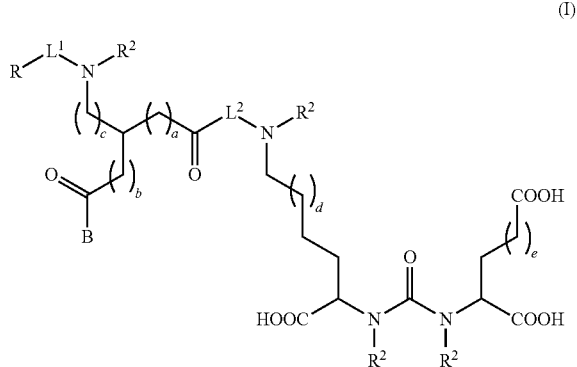

20 Claims, No Drawings

ALBUMIN-BINDING PSMA INHIBITORS

CROSS-REFERENCE TO RELATED APPLICATIONS

This application is the US national phase under 35 U.S.C. § 371 of International Patent Application No. PCT/US2017/063182 filed on Nov. 24, 2017, which claims the benefit of U.S. Provisional Application No. 62/425,810, filed Nov. 23, 2016.

BACKGROUND OF THE INVENTION

Field of the Invention

The present invention relates to small molecules having high affinity and specificity to prostrate-specific membrane antigen (PSMA) and methods of using them for diagnostic and therapeutic purposes.

Summary of the Related Art

Prostate-specific membrane antigen (PSMA) is uniquely overexpressed on the surface of prostate cancer cells as well as in the neovasculature of a variety of solid tumors. As a result, PSMA has attracted attention as a clinical biomarker for detection and management of prostate cancer. Generally, these approaches utilize an antibody specifically targeted at PSMA to direct imaging or therapeutic agents. For example, ProstaScint (Cytogen, Philadelphia, Pa.), which has been approved by the FDA for the detection and imaging of prostate cancer, utilizes an antibody to deliver a chelated radioisotope (Indium-111). However, it is now recognized that the ProstaScint technology is limited to the detection of dead cells and therefore its clinical relevance is questionable.

The success of cancer diagnosis and therapy using antibodies is limited by challenges such as immunogenicity and poor vascular permeability. In addition, large antibodies bound to cell-surface targets present a barrier for subsequent binding of additional antibodies at neighboring cell-surface sites resulting in a decreased cell-surface labeling.

In addition to serving as a cell-surface target for antibodies delivering diagnostic or therapeutic agents, a largely overlooked and unique property of PSMA is its enzymatic activity. That is, PSMA is capable of recognizing and processing molecules as small as dipeptides. Despite the existence of this property, it has been largely unexplored in terms of the development of novel diagnostic and therapeutic strategies. There are a few recent examples in the literature that have described results in detecting prostate cancer cells using labeled small-molecule inhibitors of PSMA.

SUMMARY OF THE INVENTION

Provided herein are imaging diagnostics and therapeutics for prostate cancer that capitalize on the potency and specific affinity of small-molecule inhibitors to PSMA. The diagnostic agents can be used to monitor and stratify patients for treatment with appropriate therapeutic agents.

Accordingly, in one aspect the present disclosure provides compounds of Formula (I)

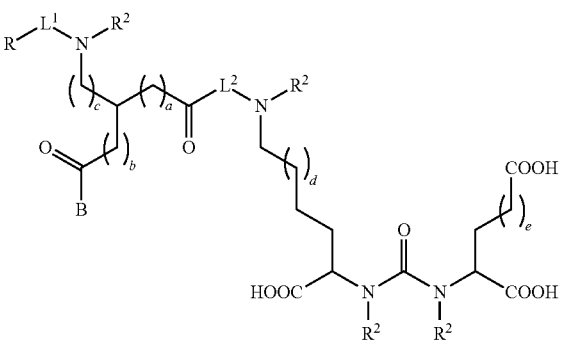

(I)

or that is a pharmaceutically acceptable salt thereof, wherein $L^1$ and $L^2$ are each independently a covalent bond or a divalent linking group;

R is a detectable label or therapeutic drug;

B is an albumin binding moiety;

each a, b and c is independently 0, 1, 2 or 3; and each $R^2$ is independently hydrogen, $C_1$-$C_6$ alkyl or a protecting group.

In another aspect, the present disclosure provides compounds of Formula (Ia)

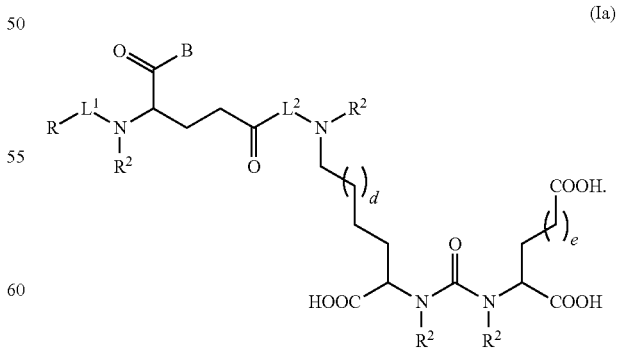

(Ia)

In another aspect, the present disclosure provides compounds of Formula (Ib)

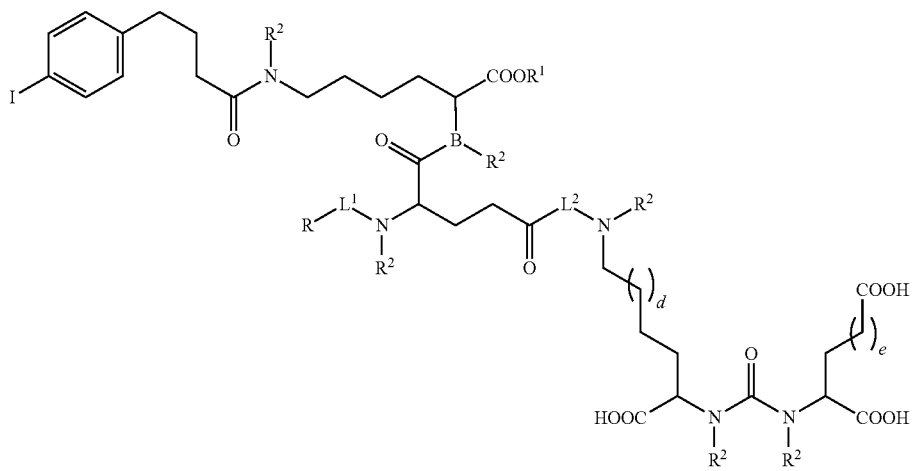

or a pharmaceutically acceptable salt thereof, wherein
- $L^1$ and $L^2$ are each independently a covalent bond or a divalent linking group;
- R is a or therapeutic drug or chelating agent optionally chelating a therapeutic radioisotope or a PET-active, SPECT-active, or MRI-active radioisotope; and
- each $R^1$ and $R^2$ are each independently hydrogen, $C_1$-$C_6$ alkyl or a protecting group.

In another aspect, the present disclosure provides compounds of Formula (Ic)

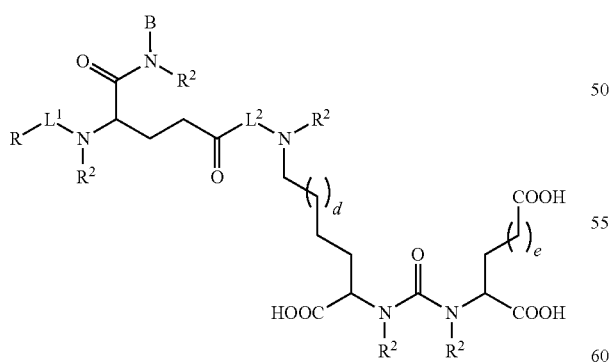

or a pharmaceutically acceptable salt thereof, wherein d and e are each independently 0, 1, 2, 3, 4 or 5.

In another aspect, the present disclosure provides compounds of Formula (Id)

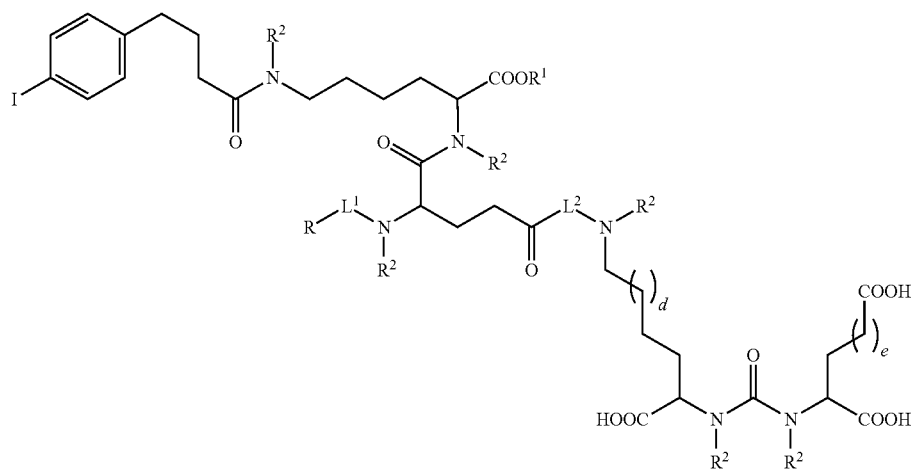

(Id)

or a pharmaceutically acceptable salt thereof, wherein d and e are each independently 0, 1, 2, 3, 4 or 5.

In another aspect the present disclosure provides pharmaceutical compositions comprising a compound of the preceding aspect and a pharmaceutically acceptable carrier.

In another aspect the present disclosure provides methods for imaging one or more prostate cancer cells or tumor-associated vasculature in a patient comprising administering to the patient a compound or a pharmaceutical composition of either of the preceding aspects.

All publicly available documents recited in this application are hereby incorporated by reference in their entirety to the extent their teachings are not inconsistent with the present disclosure.

DETAILED DESCRIPTION OF THE INVENTION

In one aspect, the present disclosure provides compounds useful as PET imaging diagnostics and radiotherapeutic agents for prostate cancer that capitalize on the potency and specific affinity of small-molecule inhibitors to PSMA.

In embodiment $I_1$ of the first aspect are compounds that have structural Formula (I)

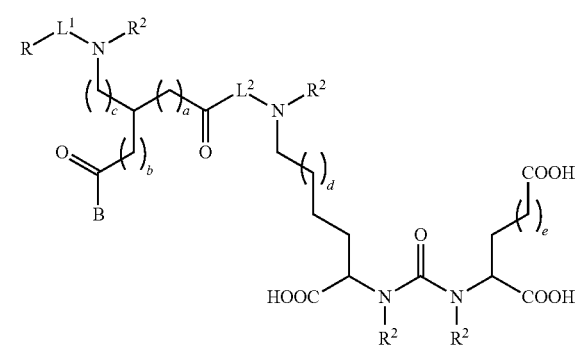

(I)

or that is a pharmaceutically acceptable salt thereof, wherein $L^1$ and $L^2$ are each independently a covalent bond or a divalent linking group;

R is a detectable label or therapeutic drug;

B is an albumin binding moiety;

each a, b and c is independently 0, 1, 2 or 3; and each $R^2$ is independently hydrogen, $C_1$-$C_6$ alkyl or a protecting group.

In embodiment $I_1$ of the first aspect are compounds that have structural Formula (Ia)

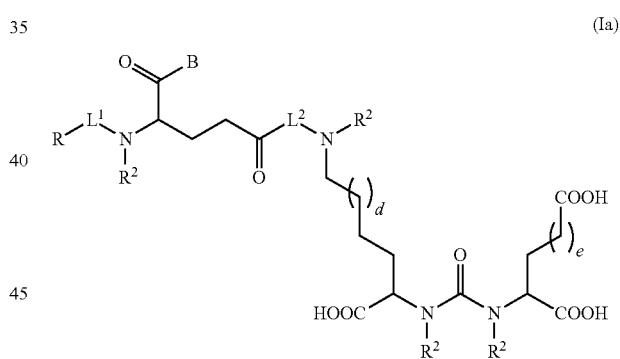

(Ia)

or that are a pharmaceutically acceptable salt thereof, wherein $L^1$ and $L^2$ are each independently a covalent bond or a divalent linking group;

R is a detectable label or therapeutic drug;

B is an albumin binding moiety; and each $R^2$ is independently hydrogen, $C_1$-$C_6$ alkyl or a protecting group.

Numerous albumin binding moieties useful in the compounds and methods of the invention are known in the art and include, for example, moieties disclosed and referred to in the following (each of which are incorporated herein by reference): Ghuman et al., "Structural Basis of the Drug-binding Specificity of Human Serum Albumin," *Journal of Molecular Biology*, 353(1), 14 Oct. 2005, 38-52; Carter, D. C. and Ho, J. X. (1994) "Structure of serum albumin," *Adv. Protein Chem.*, 45, 153-203; Curry, S. (2009) "Lessons from the crystallographic analysis of small molecule binding to human serum albumin," *Drug Metab. Pharmacokinet.*, 24, 342-357; Kratochwil, N. A. et al. (2002) "Predicting plasma protein binding of drugs: a new approach," *Biochem. Pharmacol.*, 64, 1355-1374; Zsila et al. (2011) "Evaluation of drug-human serum albumin binding interactions with support vector machine aided online automated docking," *Bioimformatics* 27(13), 1806-1813; Elsadek et al., *J Control Release.*, "Impact of albumin on drug delivery—new applications on the horizon," 2012 Jan. 10; 157(1):4-28; Nemati et al., "Assessment of Binding Affinity between Drugs and Human Serum Albumin Using Nanoporous Anodic Alumina Photonic Crystals," Anal Chem. 2016 Jun. 7; 88(11):5971-80; Larsen, M. T. et al., "Albumin-based drug delivery: harnessing nature to cure disease," *Mol Cell. Ther.*, 2016, Feb. 27; 4:3; Howard, K. A., "Albumin: the next-generation delivery technology," *Ther. Deliv.*, 2015, March; 6(3):265-8; Sleep D. et al., "Albumin as a versatile platform for drug half-life extension," *Biochim. Biophys. Acta.*, 2013, December; 1830(12):5526-34; Sleep, D., "Albumin and its application in drug delivery," *Expert Opin. Drug Deliv.*, 2015, May; 12(5):793-812; Qi, J et al., "Multidrug Delivery Systems Based on Human Serum Albumin for Combination Therapy with Three Anticancer Agents," *Mol. Pharm.*, 2016 Aug. 8., Article ASAP Epub ahead of print; Karimi M. et al., "Albumin nanostructures as advanced drug delivery systems," *Expert Opin. Drug Deliv.*, 2016 Jun. 3:1-15, Article ASAP Epub ahead of print; Gou, Y. et al., "Developing Anticancer Copper(II) Pro-drugs Based on the Nature of Cancer Cells and the Human Serum Albumin Carrier IIA Subdomain," *Mol. Pharm.*, 2015 Oct. 5; 12(10):3597-609; Yang, F. et al., "Interactive associations of drug-drug and drug-drug-drug with IIA subdomain of human serum albumin," *Mol. Pharm.*, 2012 Nov. 5; 9(11):3259-65; Agudelo, D. et al., "An overview on the delivery of antitumor drug doxorubicin by carrier proteins," *Int. J. Biol. Macromol.*, 2016, July; 88:354-60; Durandin, N. A. et al., "Quantitative parameters of complexes of tris(1-alkylindol-3-yl)methylium salts with serum albumin: Relevance for the design of drug candidates," *J. Photochem. Photobiol. B.*, 2016 Jul. 18; 162:570-576; Khodaei, A. et al., "Interactions Between Sirolimus and Anti-Inflammatory Drugs: Competitive Binding for Human Serum Albumin," *Adv. Pharm. Bull.*, 2016, June; 6(2):227-33; Gokara, M. et al., "Unravelling the Binding Mechanism and Protein Stability of Human Serum Albumin while Interacting with Nefopam Analogues: A Biophysical and Insilco approach," *J. Biomol. Struct. Dyn.*, 2016 Jul. 25:1-44; Zhang, H. et al., "Affinity of miriplatin to human serum albumin and its effect on protein structure and stability," *Int. J. Biol. Macromol.*, 2016 Jul. 22; 92:593-599; Bijelic, A. et al., "X-ray Structure Analysis of Indazolium trans-[Tetrachlorobis(1H-indazole)ruthenate(III)] (KP1019) Bound to Human Serum Albumin Reveals Two Ruthenium Binding Sites and Provides Insights into the Drug Binding Mechanism," *J. Med. Chem.*, 2016 Jun. 23; 59(12):5894-903; Fasano, M. et al., "The Extraordinary Ligand Binding Properties of Human Serum Albumin," *Life*, 57(12): 787-796. Albumin binding is also utilized in many known drugs, such as warfarin, lorazepam, and ibuprofen.

In some embodiments, the albumin binding moiety can be a bicyclic albumin binding moiety, such as that described in Pollaro, L. et al. "Bicyclic Peptides Conjugated to an Albumin-Binding Tag Diffuse Efficiently into Solid Tumors" Mol. Cancer Ther. 2015, 14, 151-161.

In some embodiments, the albumin binding moiety can be an albumin binding Fab, such as that described in Dennis, M. S. et al. "Imaging Tumors with an Albumin-Binding Fab, a Novel Tumor-Targeting Agent" Cancer Res. 2007, 67, 254-261.

In some embodiments, the albumin binding moiety can be an Evans Blue Dye, such as that described in Jacobson, O. et al. "Albumin-Binding Evans Blue Derivatives for Diagnostic Imaging and Production of Long-Acting Therapeutics" Bioconjugate Chem., 2016, 27 (10), 2239-2247; and Chen, H. et al. "Chemical Conjugation of Evans Blue Derivative: A Strategy to Develop Long-Acting Therapeutics through Albumin Binding" Theranostics., 2016 6 (2), 243-253.

In some embodiments according to the invention, B is

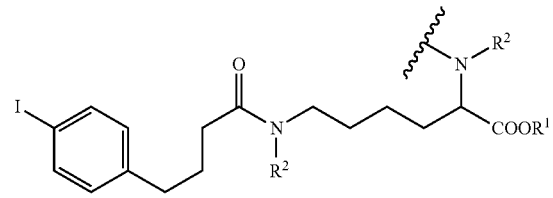

In embodiment $I_2$ are compounds that are of Formula (Ib)

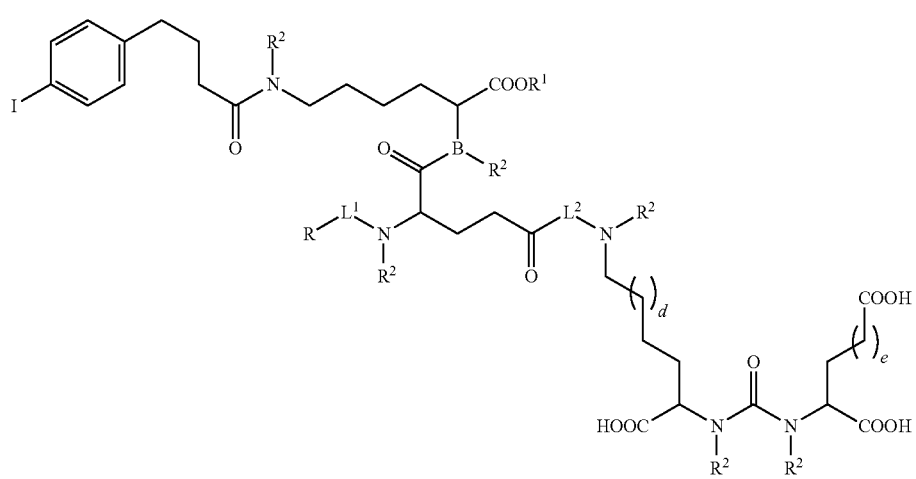

(Ib)

or that are a pharmaceutically acceptable salt thereof, wherein

L$^1$ and L$^2$ are each independently a covalent bond or a divalent linking group;

R is a detectable label or therapeutic drug;

B is an albumin binding moiety; and each R$^2$ is independently hydrogen, C$_1$-C$_6$ alkyl or a protecting group.

In embodiment I$_3$ are compounds that are of Formula (Ic)

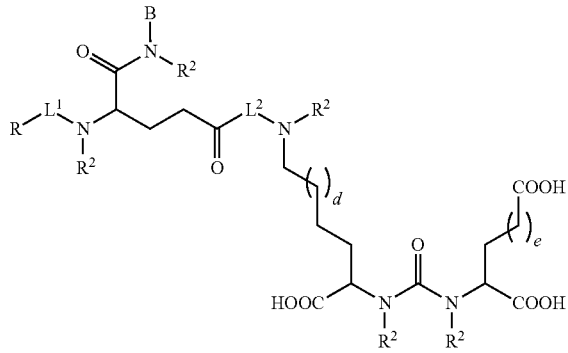

(Ic)

or that are a pharmaceutically acceptable salt thereof, wherein

L$^1$ and L$^2$ are each independently a covalent bond or a divalent linking group;

R is a detectable label or therapeutic drug;

B is an albumin binding moiety;

each R$^2$ is independently hydrogen, C$_1$-C$_6$ alkyl or a protecting group; and d and e are each independently 1, 2, 3, 4 or 5.

In embodiment I$_4$ are compounds that are of Formula (Id)

Divalent linking groups include groups of the formula, —(C$_0$-C$_{10}$ alkyl-Q)$_{0-1}$-C$_0$-C$_{10}$ alkyl-, wherein Q is a bond, aryl (e.g., phenyl), heteroaryl, C$_3$-C$_8$ cycloalkyl, or heterocyclyl; and no more than one methylene in each alkyl group is optionally and independently replaced by —O—, —S—, —N(R$^{00}$)—, —C(H)=C(H)—, —C≡C—, —C(O)—, —S(O)—, —S(O)$_2$—, —P(O)(OR$^{00}$)—, —OP(O)(OR$^{00}$)—, —P(O)(OR$^{00}$)O—, —N(R$^{00}$)P(O)(OR$^{00}$)—, —P(O)(OR$^{00}$)N(R$^{00}$)—, —OP(O)(OR$^{00}$)O—, —OP(O)(OR$^{00}$)N(R$^{00}$)—, —N(R$^{00}$)P(O)(OR$^{00}$)O—, —N(R$^{00}$)P(O)(OR$^{00}$)N(R$^{00}$)—, —C(O)O—, —C(O)N(R$^{00}$)—, —OC(O)—, —N(R$^{00}$)C(O)—, —S(O)O—, —OS(O)—, —S(O)N(R$^{00}$)—, —N(R$^{00}$)S(O)—, —S(O)$_2$O—, —OS(O)$_2$—, —S(O)$_2$N(R$^{00}$)—, —N(R$^{00}$)S(O)$_2$—, OC(O)O—, —OC(O)N(R$^{00}$)—, —N(R$^{00}$)C(O)O—, —N(R$^{00}$)C(O)N(R$^{00}$)—, —OS(O)O—, —OS(O)N(R$^{00}$)—, —N(R$^{00}$)S(O)O—, —N(R$^{00}$)S(O)N(R$^{00}$)—, —OS(O)$_2$O—, —OS(O)$_2$N(R$^{00}$)—, —N(R$^{00}$)S(O)$_2$O—, or —N(R$^{00}$)S(O)$_2$N(R$^{00}$)—, wherein each R$^{00}$ is independently hydrogen or C$_1$-C$_6$ alkyl.

Divalent linking groups may also include peptides comprising natural and unnatural amino acids of 1-10 residues.

In embodiment I$_5$, the divalent linking group is selected from one of the following groups of the formula, wherein in each instance the end marked by * is attached to the chelating agent:

(a) *—(OCH$_2$CH$_2$)$_n$—, wherein n is 1-20 (e.g., 4-12, or 4, or 8, or 12);

(b) —(C(O)—(CH$_2$)$_{0-1}$—CH(R$^1$)N(R$^2$))$_m$—*, wherein m is 1-8;

each R$^1$ is independently the side chain of a natural or unnatural amino acid (e.g., each R$^1$ is independently hydrogen, C$_1$-C$_6$alkyl, aryl, heteroaryl, arylC$_1$-C$_6$alkyl, or heteroarylC$_1$-C$_6$alkyl, wherein the alkyl, arylalkyl, and heteroarylalkyl groups are optionally substituted with 1, 2, 3, 4, or 5 R$^{11}$ groups, wherein each R$^{11}$ is independently halo, (Id)

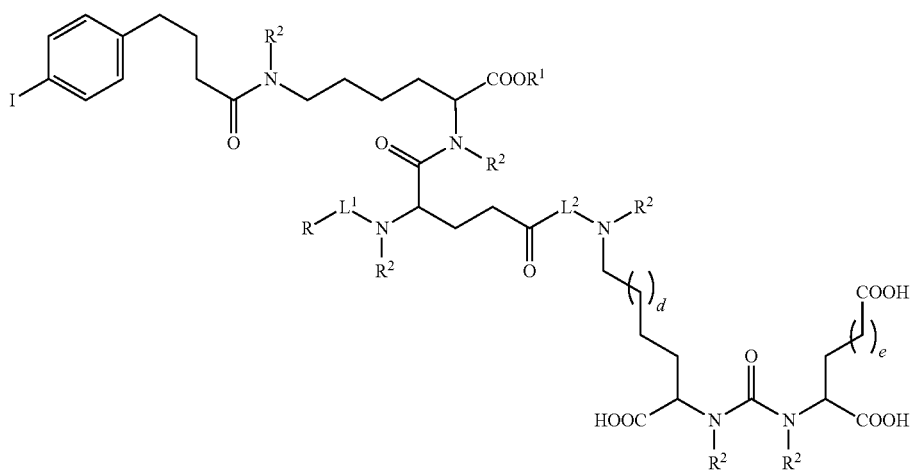

or that are a pharmaceutically acceptable salt thereof, wherein

L$^1$ and L$^2$ are each independently a covalent bond or a divalent linking group;

R is a detectable label or therapeutic drug;

each R$^2$ is independently hydrogen, C$_1$-C$_6$ alkyl or a protecting group; and d and e are each independently 0, 1, 2, 3, 4 or 5.

cyano, —OR$^{12}$, —SR$^{12}$, —N(R$^{12}$)$_2$, —C(O)OR$^{12}$, —C(O)N(R$^{12}$)$_2$, —N(R$^{12}$)C(=NR$^{12}$)N(R$^{12}$)$_2$, or C$_1$-C$_6$alkyl, wherein each R$^{12}$ is independently hydrogen or C$_1$-C$_6$alkyl);

each R$^2$ is independently hydrogen or taken together with R$^1$ within the same residue to form a heterocyclyl (e.g., having 5-members);

(c) —(C(O)(CH$_2$)$_p$—(C(O))$_{0-1}$—NH)—*, wherein p is 1-30 (e.g., p is 1-7) (e.g., 6-aminohexanoic acid, —C(O)(CH$_2$)$_5$NH—*);

(d) —(C(O)—(CH$_2$)$_r$-phenyl-(G)$_{0-1}$-(CH$_2$)$_q$—(C(O))$_{0-1}$—NH)—*, wherein G is —O— or —N(H)—, r and q are each independently 0-30 (e.g., 0-20; or 0-10, or 0-6, or 1-6)

(e.g., —(C(O)-phenyl-N(H)(CH$_2$)$_q$—(C(O))$_{0-1}$—NH)—*, wherein q is 1-6;

or —(C(O)—(CH$_2$)$_r$-phenyl-(CH$_2$)$_q$—NH)—*, wherein r and q are each independently 0-6;

or the two substituents on the phenyl are para to one another, such as in 4-aminomethylbenzoic acid,

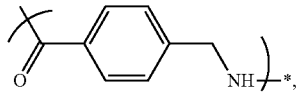

where r is 0, and q is 1; or as in 4-aminoethylbenzoic acid,

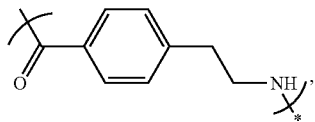

where r is 0 and q is 2); or (e)

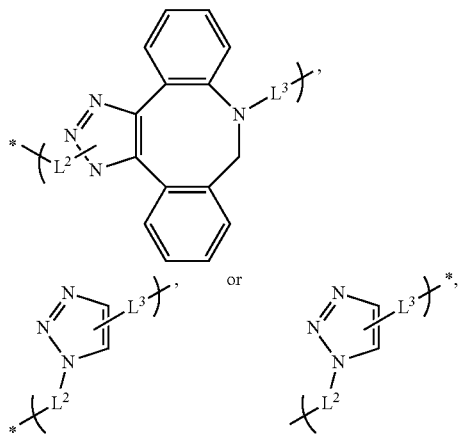

wherein
L$^2$ is —(CH$_2$)$_t$N(H)—*, wherein t is 1 to 30; and
L$^3$ is #—(CH$_2$)$_u$—C(O)—, #—(CH$_2$)$_u$—Z—Y—C(O)—, #—C(O)—(CH$_2$)$_u$—C(O)— or #—C(O)—(CH$_2$)$_u$—Z—Y—C(O)—, wherein
the # end of L$^3$ is attached to the dibenzocyclooctyne or triazolyl group above,
Y is —(CH$_2$)$_u$— or —CH$_2$CH$_2$—(OCH$_2$CH$_2$)$_n$—, wherein n is 1-20 (e.g., 4-12, or 4, or 8, or 12), and wherein the -end is attached to Z;
u is 1 to 30; and
Z is —C(O)O—, —C(O)N(R$^{oo}$)—, —OC(O)—, —N(R$^{oo}$)C(O)—, —S(O)$_2$N(R$^{oo}$)—, —N(R$^{oo}$)S(O)$_2$—, —OC(O)O—, —OC(O)N(R$^{oo}$)—, —N(R$^{oo}$)C(O)O—, or —N(R$^{oo}$)C(O)N(R$^{oo}$)—, wherein each R$^{oo}$ is independently hydrogen or C$_1$-C$_6$ alkyl;

(f)

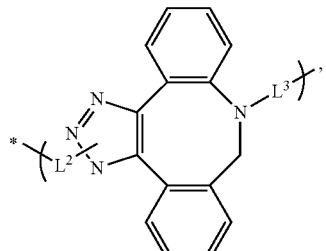

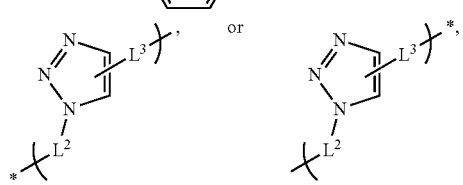

wherein
L$^2$ is —(CH$_2$)$_t$N(H)—*, wherein t is 1 to 30; and
L$^3$ is #—(CH$_2$)$_u$—C(O)—, #—(CH$_2$)$_u$—Z—Y—C(O)—, #—C(O)—(CH$_2$)$_u$—C(O)— or #—C(O)—(CH$_2$)$_u$—Z—Y—C(O)—, wherein
the # end of L$^3$ is attached to the dibenzocyclooctyne or triazolyl group above,
Y is —(CH$_2$)$_u$— or —CH$_2$CH$_2$—(OCH$_2$CH$_2$)$_n$—, wherein n is 1-20 (e.g., 4-12, or 4, or 8, or 12), and wherein the -end is attached to Z;
u is 1 to 30; and
Z is —C(O)O—, —C(O)N(R$^{oo}$)—, —OC(O)—, —N(R$^{oo}$)C(O)—, —S(O)$_2$N(R$^{oo}$)—, —N(R$^{oo}$)S(O)$_2$—, —OC(O)O—, —OC(O)N(R$^{oo}$)—, —N(R$^{oo}$)C(O)O—, or —N(R$^{oo}$)C(O)N(R$^{oo}$)—, wherein each R$^{oo}$ is independently hydrogen or C$_1$-C$_6$ alkyl;

(g)

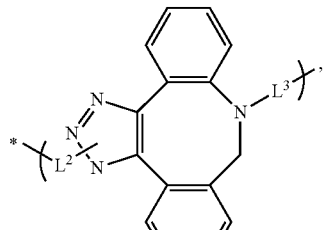

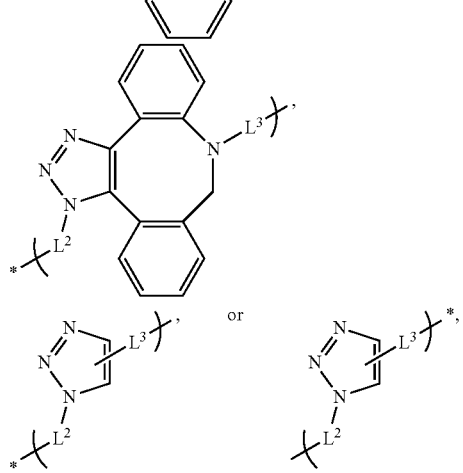

wherein

L² is —(CH₂)$_t$N(H)—*, wherein t is 1 to 30; and

L³ is #—(CH₂)$_u$—C(O)—, #—(CH₂)$_u$—Z—Y—C(O)—, #—C(O)—(CH₂)$_u$—C(O)— or #—C(O)—(CH₂)$_u$—Z—Y—C(O)—, wherein the # end of L³ is attached to the dibenzocyclooctyne or triazolyl group above, Y is —(CH₂)$_v$— or —CH₂CH₂—(OCH₂CH₂)$_n$—, wherein n is 1-20 (e.g., 4-12, or 4, or 8, or 12), and wherein the -end is attached to Z;

u is 1 to 30; and

Z is —C(O)O—, —C(O)N(R⁰⁰)—, —OC(O)—, —N(R⁰⁰)C(O)—, —S(O)₂N(R⁰⁰)—, —N(R⁰⁰)S(O)₂—, —OC(O)O—, —OC(O)N(R⁰⁰)—, —N(R⁰⁰)C(O)O—, or —N(R⁰⁰)C(O)N(R⁰⁰)—, wherein each R⁰⁰ is independently hydrogen or C₁-C₆ alkyl;

(h)

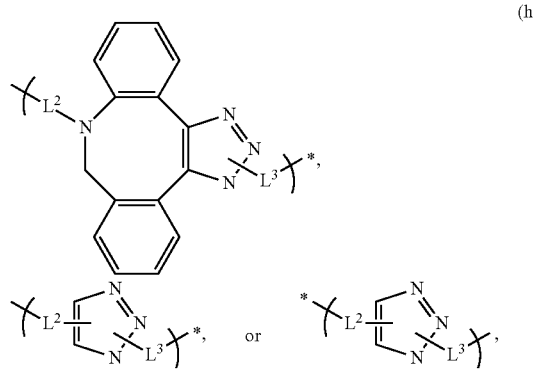

or wherein

L² is —(CH₂)$_t$N(H)—*, wherein t is 1 to 30; and

L³ is #—(CH₂)$_u$—C(O)—, #—(CH₂)$_u$—Z—Y—C(O)—, #—C(O)—(CH₂)$_u$—C(O)— or #—C(O)—(CH₂)$_u$—Z—Y—C(O)—, wherein the # end of L³ is attached to the dibenzocyclooctyne or triazolyl group above, Y is —(CH₂)$_u$— or —CH₂CH₂—(OCH₂CH₂)$_n$—, wherein n is 1-20 (e.g., 4-12, or 4, or 8, or 12), and wherein the -end is attached to Z;

u is 1 to 30; and

Z is —C(O)O—, —C(O)N(R⁰⁰)—, —OC(O)—, —N(R⁰⁰)C(O)—, —S(O)₂N(R⁰⁰)—, —N(R⁰⁰)S(O)₂—, —OC(O)O—, —OC(O)N(R⁰⁰)—, —N(R⁰⁰)C(O)O—, or —N(R⁰⁰)C(O)N(R⁰⁰)—, wherein each R⁰⁰ is independently hydrogen or C₁-C₆ alkyl;

(i)

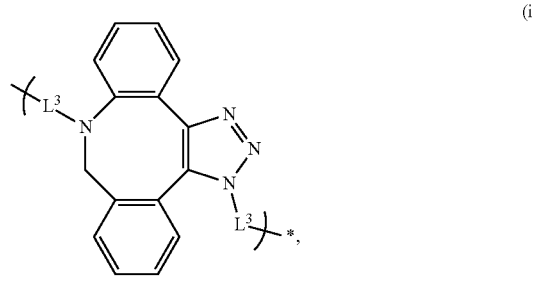

(j)

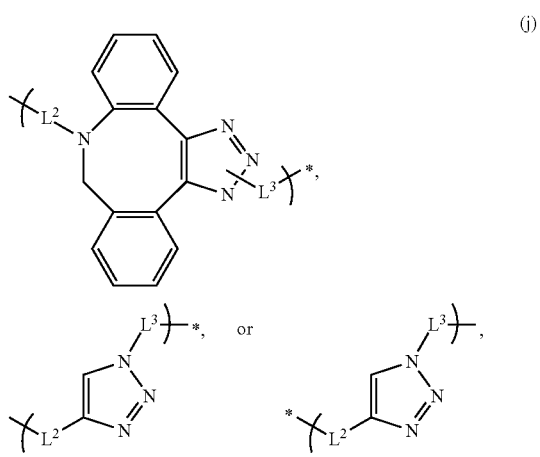

wherein

L² is —(CH₂)$_t$N(H)—*, wherein t is 1 to 30; and

L³ is #—(CH₂)$_u$—C(O)—, #—(CH₂)$_u$—Z—Y—C(O)—, #—C(O)—(CH₂)$_u$—C(O)— or #—C(O)—(CH₂)$_u$—Z—Y—C(O)—, wherein the # end of L³ is attached to the dibenzocyclooctyne or triazolyl group above, Y is —(CH₂)$_u$— or —CH₂CH₂—(OCH₂CH₂)$_n$—, wherein n is 1-20 (e.g., 4-12, or 4, or 8, or 12), and wherein the -end is attached to Z;

u is 1 to 30; and

Z is —C(O)O—, —C(O)N(R⁰⁰)—, —OC(O)—, —N(R⁰⁰)C(O)—, —S(O)₂N(R⁰⁰)—, —N(R⁰⁰)S(O)₂—, —OC(O)O—, —OC(O)N(R⁰⁰)—, —N(R⁰⁰)C(O)O—, or —N(R⁰⁰)C(O)N(R⁰⁰)—, wherein each R⁰⁰ is independently hydrogen or C₁-C₆ alkyl;

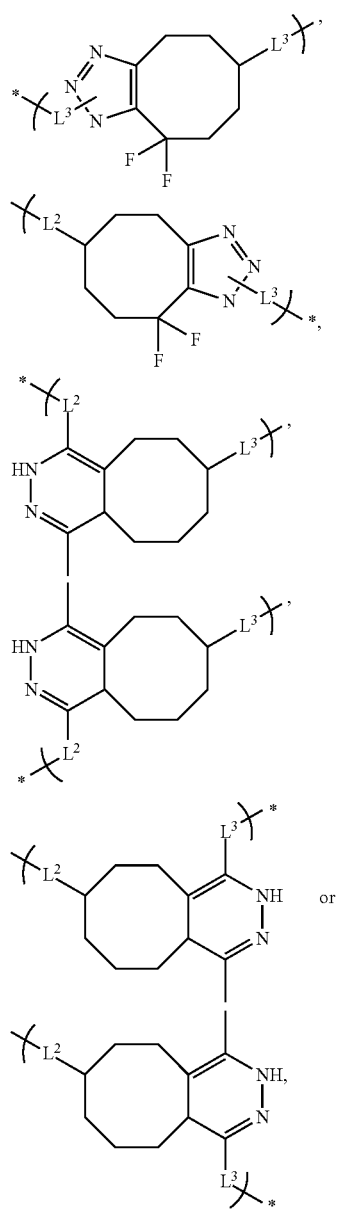
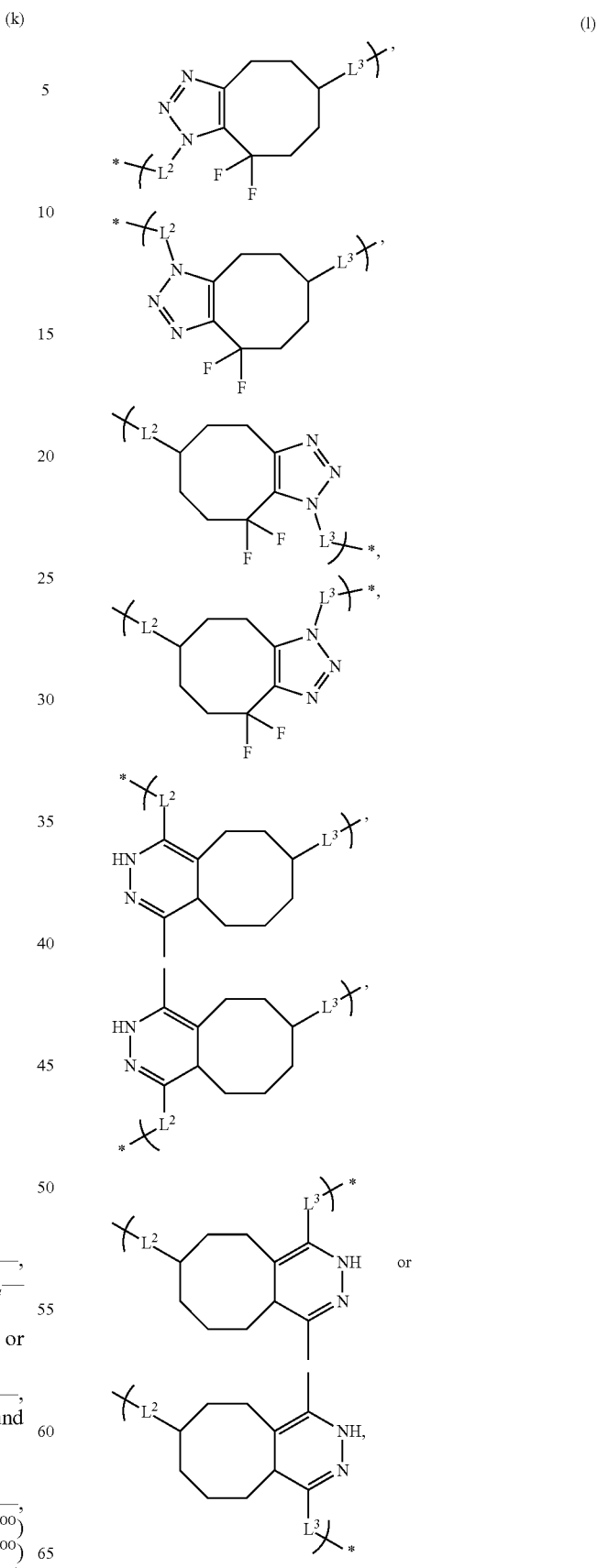

wherein

L² is —(CH₂)ₜN(H)—*, wherein t is 1 to 30; and

L³ is #—(CH₂)ᵤ—C(O)—, #—(CH₂)ᵤ—Z—Y—C(O)—, #—C(O)—(CH₂)ᵤ—C(O)— or #—C(O)—(CH₂)ᵤ—Z—Y—C(O)—, wherein the # end of L³ is attached to the dibenzocyclooctyne or triazolyl group above, Y is —(CH₂)ᵤ— or —CH₂CH₂—(OCH₂CH₂)ₙ—, wherein n is 1-20 (e.g., 4-12, or 4, or 8, or 12), and wherein the -end is attached to Z;

u is 1 to 30; and

Z is —C(O)O—, —C(O)N(R⁰⁰)—, —OC(O)—, —N(R⁰⁰)C(O)—, —S(O)₂N(R⁰⁰)—, —N(R⁰⁰)S(O)₂—, —OC(O)O—, —OC(O)N(R⁰⁰)—, —N(R⁰⁰)C(O)O—, or —N(R⁰⁰)C(O)N(R⁰⁰)—, wherein each R⁰⁰ is independently hydrogen or C₁-C₆ alkyl;

wherein
L² is —(CH₂)ₜN(H)—*, wherein t is 1 to 30; and
L³ is #—(CH₂)ᵤ—C(O)—, #—(CH₂)ᵤ—Z—Y—C(O)—, #—C(O)—(CH₂)ᵤ—C(O)— or #—C(O)—(CH₂)ᵤ—Z—Y—C(O)—, wherein
the # end of L³ is attached to the dibenzocyclooctyne or triazolyl group above,
Y is —(CH₂)ᵤ— or —CH₂CH₂—(OCH₂CH₂)ₙ—, wherein n is 1-20 (e.g., 4-12, or 4, or 8, or 12), and wherein the -end is attached to Z;
u is 1 to 30; and
Z is —C(O)O—, —C(O)N(R⁰⁰)—, —OC(O)—, —N(R⁰⁰)C(O)—, —S(O)₂N(R⁰⁰)—, —N(R⁰⁰)S(O)₂—, —OC(O)O—, —OC(O)N(R⁰⁰)—, —N(R⁰⁰)C(O)O—, or —N(R⁰⁰)C(O)N(R⁰⁰)—, wherein each R⁰⁰ is independently hydrogen or C₁-C₆ alkyl;
and (m) combinations of the preceding, wherein in each instance, the *-end is attached to the chelating agent, such as:
(i) —(CH₂CH₂O)ₙ—(C(O)(CH₂)ₚ—(C(O))₀₋₁—NH)—*, where n and p are as defined above (e.g., n is 4 and p is 6);
(ii) —(CH₂CH₂O)ₙ—(C(O)—(CH₂)₀₋₁—CH(R¹)N(R²))ₘ—*, where R¹, R², n and m are as defined above (e.g., n is 4 and m is 2);
(iii) —(CH₂CH₂O)ₙ—(C(O)—(CH₂)ᵣ-phenyl-(G)₀₋₁-(CH₂)_q—(C(O))₀₋₁—NH)—*, where G, n, q, and r are as defined above (e.g., n is 4, q is 1, and r is 0);
(iv) —(C(O)—(CH₂)₀₋₁—CH(R¹)N(R²))ₘ—(C(O)(CH₂)ₚ—(C(O))₀₋₁—NH)—*, where R¹, R², m and p are as defined above (e.g., m is 2 and p is 6);
(v) —(C(O)—(CH₂)₀₋₁—CH(R¹)N(R²))ₘ—(C(O)—(CH₂)ᵣ-phenyl-(G)₀₋₁-(CH₂)_q—(C(O))₀₋₁—NH)—*, where G, R¹, R², m, q, and r are as defined above (e.g., m is 2, q is 1, and r is 0; or m is 2, q is 2, and r is 0);
(vi) —(C(O)(CH₂)ₚ—(C(O))₀₋₁—NH)—(C(O)—(CH)ᵣ-phenyl-(G)₀₋₁-(CH₂)_q—(C(O))₀₋₁—NH)—*, where G, p, q, and r are as defined above (e.g., p is 6, q is 1, and r is 0; p is 6, q is 2, and r is 0; p is 5, q is 1, and r is 0; or p is 5, q is 2, and r is 0);
(vii) —(C(O)(CH₂)ₚ—(C(O))₀₋₁—NH)—(C(O)—(CH₂(R¹)N(R²))ₘ—*, where R¹, R², m and p are as defined above (e.g., m is 2 and p is 6);
(viii) —(C(O)—(CH₂)ᵣ-phenyl-(G)₀₋₁-(CH₂)_q—(C(O))₀₋₁—NH)—(C(O)—(CH₂)₀₋₁—CH(R¹)N(R²))ₘ—*, where G, R¹, R², m, q, and r are as defined above (e.g., m is 2, q is 1, and r is 0; or m is 2, q is 2, and r is 0);
(ix) —(C(O)—(CH₂)ᵣ-phenyl-(G)₀₋₁-(CH₂)_q—(C(O))₀₋₁—NH)—(C(O)(CH₂)ₚ—(C(O))₀₋₁—NH)—*, where G, p, q, and r are as defined above (e.g., p is 6, q is 1, and r is 0; p is 6, q is 2, and r is 0; p is 5, q is 1, and r is 0; or p is 5, q is 2, and r is 0);
(x) —(C(O)(CH₂)ₚ—(C(O))₀₋₁—NH)—(CH₂CH₂O)ₙ—*, where n and p are as defined above (e.g., n is 4 and p is 6);
(xi) —(C(O)—(CH₂)₀₋₁—CH(R¹)N(R²))ₘ—(CH₂CH₂O)ₙ—*, where R¹, R², n and m are as defined above (e.g., n is 4 and m is 2); and
(xii) —(C(O)—(CH₂)ᵣ-phenyl-(G)₀₋₁-(CH₂)_q—(C(O))₀₋₁—NH)—(CH₂CH₂O)ₙ—*, where G, n, q, and r are as defined above (e.g., n is 4, q is 1, and r is 0; n is 4, q is 2, and r is 0);
(xiii) —(C(O)(CH₂)ₚN(H)C(O)(CH₂)ₚNH—)*, where each p is independently as defined above (e.g., each p is 5, —C(O)(CH₂)₅NH—C(O)(CH₂)₅NH—*);
(xiv) a covalent bond.

In embodiment I₅ₐ, the divalent linking group is selected from one of the following groups of the formula, wherein in each instance, the *-end is attached to the chelating agent:
(xv) —(C(O)(CH₂)ₚ—(C(O))₀₋₁—NH)—*, wherein p is 1-7, (e.g., 6-aminohexanoic acid, —C(O)(CH₂)₅NH—*);
(xvi) —(C(O)—(CH₂)ᵣ-phenyl-(G)₀₋₁-(CH₂)_q—(C(O))₀₋₁—NH)—*, wherein G is —N(H)—, r is 0-6 (e.g., 0-3, or 0-2, or 0, or 1, or 2, or 1-6), q is 1-6 (e.g., 1-3, or 1-2, or 1, or 2) (e.g., the two substituents on the phenyl are para to one another, such as in 4-aminomethylbenzoic acid,

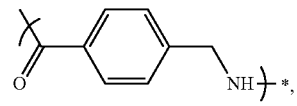

where r is 0 and q is 1; or as in 4-aminoethylbenzoic acid,

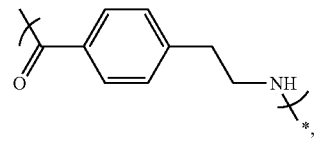

where r is 0 and q is 2); or
(xvii) —(C(O)(CH₂)ₚ—(C(O))₀₋₁—NH)—(C(O)—(CH₂)ᵣ-phenyl-(G)₀₋₁-(CH₂)_q—(C(O))₀₋₁—NH)—*, where G, p, q, and r are as defined above (e.g., p is 6, q is 1, and r is 0; p is 6, q is 2, and r is 0; p is 5, q is 1, and r is 0; or p is 5, q is 2, and r is 0);
(xviii) —(C(O)—(CH₂)ᵣ-phenyl-(G)₀₋₁-(CH₂)_q—(C(O))₀₋₁—NH)—(C(O)(CH₂)ₚ—(C(O))₀₋₁—NH)—*, where G, p, q, and r are as defined above (e.g., p is 6, q is 1, and r is 0; p is 6, q is 2, and r is 0; p is 5, q is 1, and r is 0; or p is 5, q is 2, and r is 0);
(xix) —(C(O)(CH₂)ₚN(H)C(O)(CH₂)ₚNH—)*, where each p is independently as defined above (e.g., each p is 5, —C(O)(CH₂)₅NH—C(O)(CH₂)₅NH—);
(xx) a covalent bond.

In embodiment I₅ᵦ, the divalent linking group is selected from one of the following groups of the formula, wherein in each instance, the *-end is attached to the chelating agent:
(xxi) —(C(O)(CH₂)ₚ—(C(O))₀₋₁—NH)—*, wherein p is 4-6, (e.g., 6-aminohexanoic acid, —C(O)(CH₂)₅NH—*);
(xxii) —(C(O)—(CH₂)ᵣ-phenyl-(G)₀₋₁-(CH₂)_q—(C(O))₀₋₁—NH)—*, wherein G is —N(H)—, r is 0-6 and q is 1-3 (e.g., the two substituents on the phenyl are para to one another, such as in 4-aminomethylbenzoic acid,

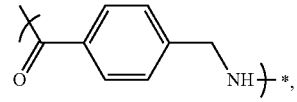

where q is 1; or as in 4-aminoethylbenzoic acid,

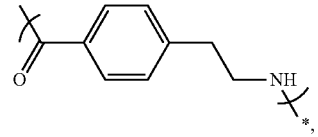

where q is 2); or (xxiii) —(C(O)(CH$_2$)$_p$—(C(O))$_{0-1}$—NH)—(C(O)—(CH$_2$)$_r$-phenyl-(G)$_{0-1}$-(CH$_2$)$_q$—(C(O))$_{0-1}$—NH)—*, where p, q, and r are as defined above (e.g., p is 6, q is 1, and r is 0; p is 6, q is 2, or r is 0; p is 5, q is 1, and r is 0; or p is 5, q is 2, and r is 0);

(xxiv) —(C(O)—(CH$_2$)$_r$-phenyl-(G)$_{0-1}$-(CH$_2$)$_q$—(C(O))$_{0-1}$—NH)—(C(O)(CH$_2$)$_p$—(C(O))$_{0-1}$—NH)—*, where G, p, q, and r are as defined above (e.g., p is 6, q is 1, and r is 0; p is 6, q is 2, and r is 0; p is 5, q is 1, and r is 0; or p is 5, q is 2, and r is 0);

(xxv) —(C(O)(CH$_2$)$_p$N(H)C(O)(CH$_2$)$_p$NH—)*, where each p is independently as defined above (e.g., each p is 5, —C(O)(CH$_2$)$_5$NH—C(O)(CH$_2$)$_5$NH—*);

(xxvi) a covalent bond.

In embodiment I$_{5c}$, the divalent linking group is selected from one of the following groups of the formula, wherein in each instance, the *-end is attached to the chelating agent:

(i) —C(O)(CH$_2$)$_5$NH—*;

(ii)
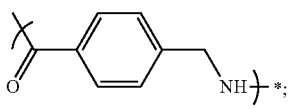

(iii)
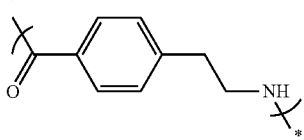

(iv)
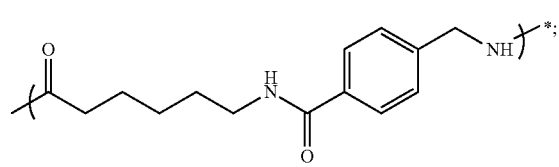

(v)
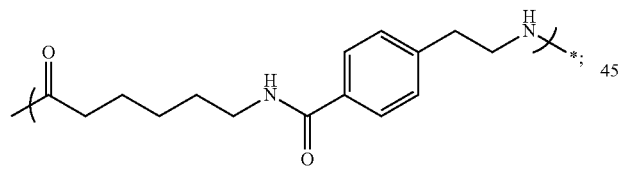

(vi) —C(O)(CH$_2$)$_5$NH—C(O)(CH$_2$)$_5$NH—*;
(vii) C$_1$-C$_6$alkyl;
(viii) C$_1$-C$_6$alkyl-NH—;
(ix) a covalent bond.

In embodiment I$_6$, L$^1$ is a moiety of the formula L$^{1A}$-NH—CH$_2$CH$_2$—(OCH$_2$CH$_2$-)$_y$—C(O)—, wherein
y is 1, 2, 3, 4, 5, 6, 7, 8, 9, 10, 11 or 12; and
L$^{1A}$ is a divalent linking group.

In embodiment I$_{6a}$, the compounds are of embodiment I$_6$ wherein y is selected from one of the following groups (1a)-(1x):

| (1a) | 1, 2, 3, 4, 5, 6, 7, 8, 9, 10, 11 or 12. | (1b) | 1, 2, 3, 4, 5, 6, 7, 8, 9 or 10. |
|---|---|---|---|
| (1c) | 1, 2, 3, 4, 5, 6, 7 or 8. | (1d) | 1, 2, 3, 4, 5 or 6. |
| (1e) | 1, 2, 3 or 4. | (1f) | 1 or 2. |
| (1g) | 6, 7, 8, 9, 10, 11 or 12. | (1h) | 6, 7, 8, 9 or 10. |
| (1i) | 3, 4, 5, 6, 7 or 8. | (1j) | 2, 4, 6, 8, 10 or 12. |
| (1k) | 2, 4, 6 or 8. | (1l) | 1, 3, 5, 7, 9 or 11. |
| (1m) | 1. | (1n) | 2. |
| (1o) | 3. | (1p) | 4. |
| (1q) | 5. | (1r) | 6. |
| (1s) | 7. | (1t) | 8. |
| (1u) | 9. | (1v) | 10. |
| (1w) | 11. | (1x) | 12. |

In embodiment I$_7$, the compounds are of embodiment I$_6$, wherein L$^{1A}$ is

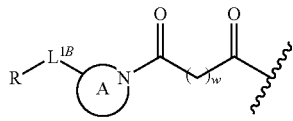

wherein
w is 1, 2, 3, 4, 5 or 6;
ring A is heterocyclic;
and L$^{1B}$ is a divalent linker.

In embodiment I$_{7a}$, the compounds are of embodiment I$_7$ wherein L$^{1B}$ is C$_1$-C$_6$alkyl-NH—.

In embodiment I$_{7b}$, the compounds are of embodiment I$_7$ wherein L$^{1A}$ is

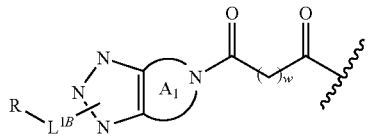

wherein
w is 1, 2, 3, 4, 5 or 6;
ring A$_1$ is heterocyclic; and
L$^{1B}$ is a divalent linker.

In embodiment I$_{7c}$, the compounds are of embodiment I$_{7b}$ wherein L$^{1B}$ is C$_1$-C$_6$alkyl-NH—.

In embodiment I$_{7d}$, the compounds are of embodiment I$_7$, wherein L$^{1A}$ is

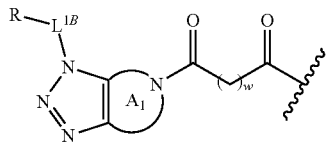

wherein
w is 1, 2, 3, 4, 5 or 6;
ring A$_1$ is heterocyclic; and
L$^{1B}$ is a divalent linker.

In embodiment I$_{7e}$, the compounds are of embodiment I$_{7d}$ wherein L$^{1B}$ is C$_1$-C$_6$alkyl-NH—.

In embodiment $I_{7f}$, the compounds are of embodiment $I_7$, wherein $L^{1A}$ is

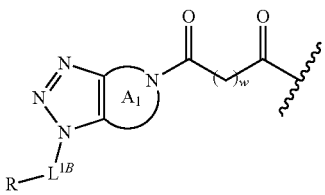

wherein
w is 1, 2, 3, 4, 5 or 6;
ring $A_1$ is heterocyclic; and
$L^{1B}$ is a divalent linker.

In embodiment $I_{7g}$, the compounds are of embodiment $I_{7f}$ wherein $L^{1B}$ is $C_1$-$C_6$alkyl-NH—.

In embodiment $I_{7h}$, the compounds are of embodiment $I_7$, wherein $L^{1A}$ is

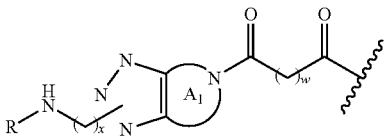

wherein
x is 0, 1, 2, 3, 4, 5 or 6;
w is 1, 2, 3, 4, 5 or 6; and
ring $A_1$ is heterocyclic.

In embodiment $I_{7i}$, the compounds are of embodiment $I_{7h}$, wherein $L^{1A}$ is

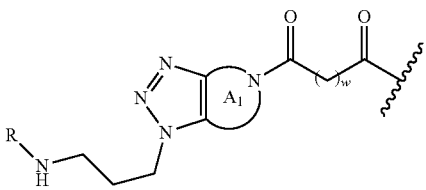

wherein
w is 1, 2, 3, 4, 5 or 6; and
ring $A_1$ is heterocyclic.

In embodiment $I_{7j}$, the compounds are of embodiment $I_7$, wherein $L^{1A}$ is

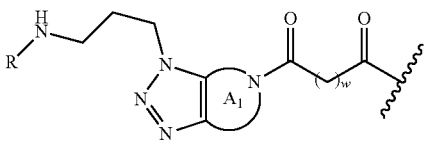

wherein
w is 1, 2, 3, 4, 5 or 6; and
ring $A_1$ is heterocyclic.

In embodiment $I_{7k}$, the compounds are of any of embodiments $I_{7a-I7j}$, wherein w is selected from one of the following groups (4a)-(4p):

| | | | |
|---|---|---|---|
| (4a) | 1, 2, 3, 4, 5 or 6. | (4b) | 1, 2, 3, 4 or 5. |
| (4c) | 1, 2, 3 or 4. | (4d) | 1, 2 or 3. |
| (4e) | 1 or 2. | (4f) | 2, 3, 4, 5 or 6. |
| (4g) | 2, 3, 4 or 5. | (4h) | 2, 3 or 4. |
| (4i) | 2 or 3 | (4j) | 3 or 4. |
| (4k) | 1. | (4l) | 2. |
| (4m) | 3. | (4n) | 4. |
| (4o) | 5. | (4p) | 6. |

In embodiment $I_{7l}$, the compounds are of embodiment $I_7$, wherein $L^{1A}$ is

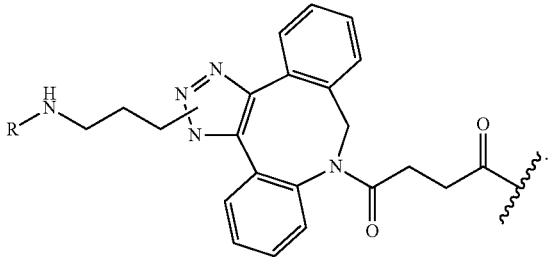

In embodiment $I_{7m}$, the compounds are of embodiment $I_7$, wherein $L^{1A}$ is

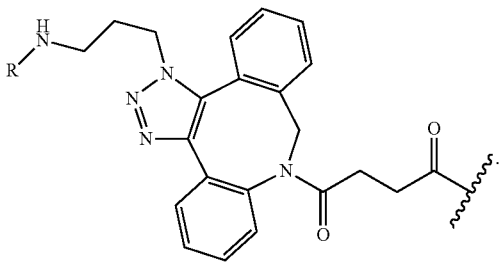

In embodiment $I_{7n}$, the compounds are of embodiment $I_7$, wherein $L^{1A}$ is

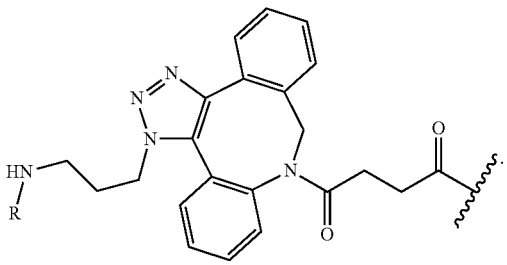

In embodiment $I_8$, $L^2$ is a group of the formula

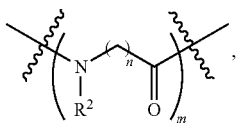

wherein
m is 1, 2, 3, or 4;
each n is independently 1, 2, 3, 4, 5, 6, 7, 8, 9, 10, 11 or 12;

provided that m·(n+2) is greater than or equal to 3 and less than or equal to 21; or a group of the formula

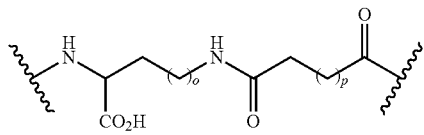

wherein o and p are each independently 0, 1, 2, 3, 4, 5, 6, 7, 8, 9, 10, 11 or 12;
or a group of the formula

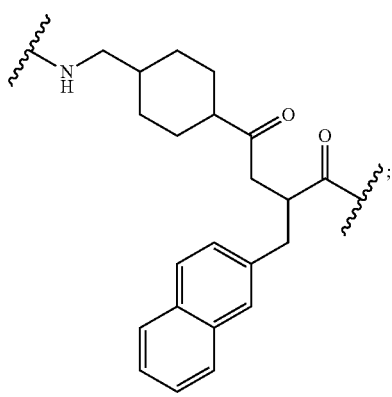 [SMILES: *NCC1CCC(C(=O)CC(Cc2ccc3ccccc3c2)C(*)=O)CC1]

or a group of the formula

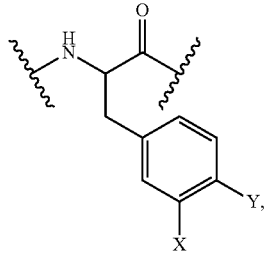

wherein X and Y are each independently hydrogen, halogen, hydroxy or alkoxy; or a combination thereof.

In embodiment $I_{8a}$, the compounds are of embodiment $I_8$ wherein m is selected from one of the following groups (2a)-(2o):

| | | | | | | | | | |
|---|---|---|---|---|---|---|---|---|---|
| (2a) | 1, 2, 3 or 4. | (2b) | 1, 2 or 3. | (2c) | 1 or 2. | (2d) | 1. | (2e) | 2, 3 or 4. |
| (2f) | 1 or 3. | (2g) | 2 or 4. | (2h) | 1 or 2. | (2i) | 2 or 3. | (2j) | 3 or 4. |
| (2k) | 1 or 4. | (2l) | 1. | (2m) | 2. | (2n) | 3. | (2o) | 4. |

In embodiment $I_{8b}$, the compounds are of embodiment $I_8$ or $I_{8a}$ wherein each n, o and p is independently selected from one of the following groups (3a)-(3x):

| | | | |
|---|---|---|---|
| (3a) | 1, 2, 3, 4, 5, 6, 7, 8, 9, 10, 11 or 12. | (3b) | 1, 2, 3, 4, 5, 6, 7, 8, 9 or 10. |
| (3c) | 1, 2, 3, 4, 5, 6, 7 or 8. | (3d) | 1, 2, 3, 4, 5 or 6. |
| (3e) | 1, 2, 3 or 4. | (3f) | 1 or 2. |
| (3g) | 6, 7, 8, 9, 10, 11 or 12. | (3h) | 6, 7, 8, 9 or 10. |
| (3i) | 3, 4, 5, 6, 7 or 8. | (3j) | 2, 4, 6, 8, 10 or 12. |
| (3k) | 2, 4, 6 or 8. | (3l) | 1, 3, 5, 7, 9 or 11. |
| (3m) | 1. | (3n) | 2. |
| (3o) | 3. | (3p) | 4. |
| (3q) | 5. | (3r) | 6. |
| (3s) | 7. | (3t) | 8. |
| (3u) | 9. | (3v) | 10. |
| (3w) | 11. | (3x) | 12. | or a pharmaceutically acceptable salt thereof.

In embodiment $I_{8c}$, the compounds are of embodiment $I_8$, wherein $L^2$ is of the formula

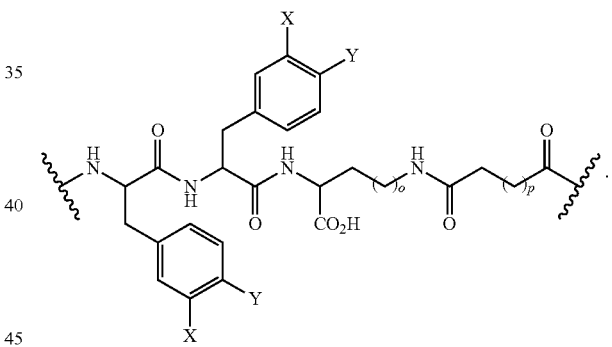

In embodiment $I_9$, the present disclosure provides compounds of Formula (Ie)

(Ie)

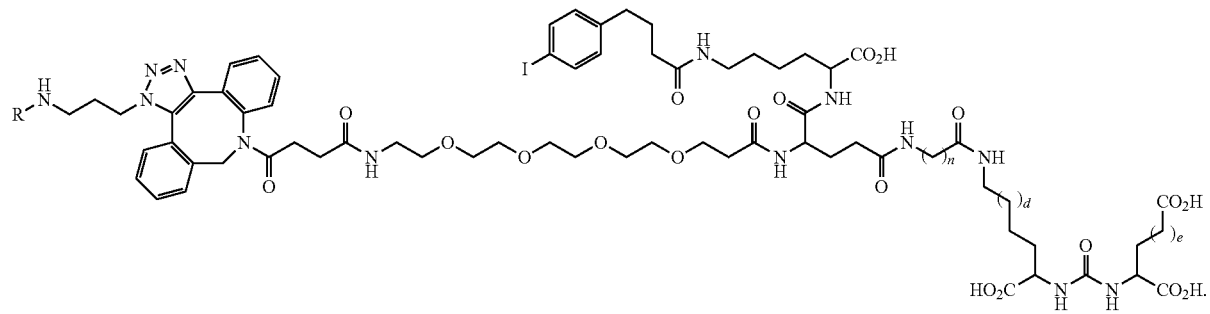

In embodiment I₁₀, the present disclosure provides compounds of Formula (If)
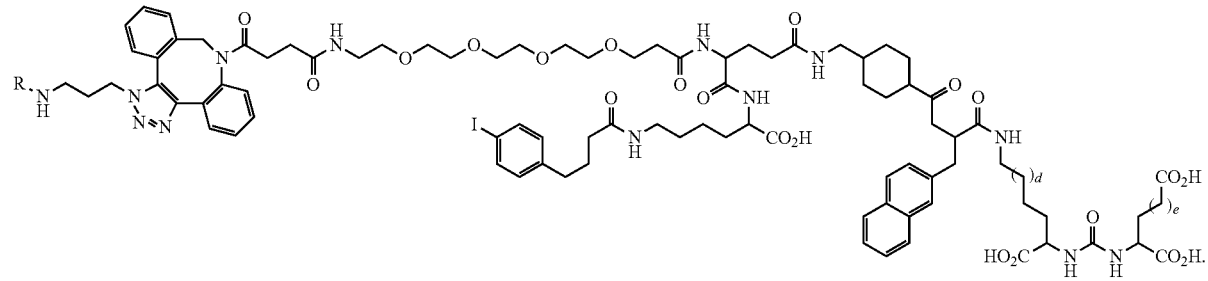
(If)
In embodiment I₁₁, the present disclosure provides compounds of Formula (Ig)
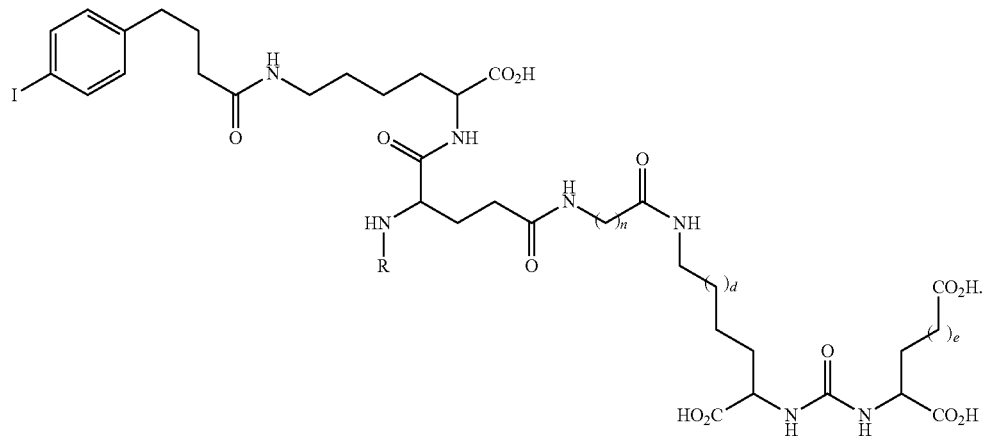
(Ig)
In embodiment I₁₂, the present disclosure provides compounds of Formula (Ih)
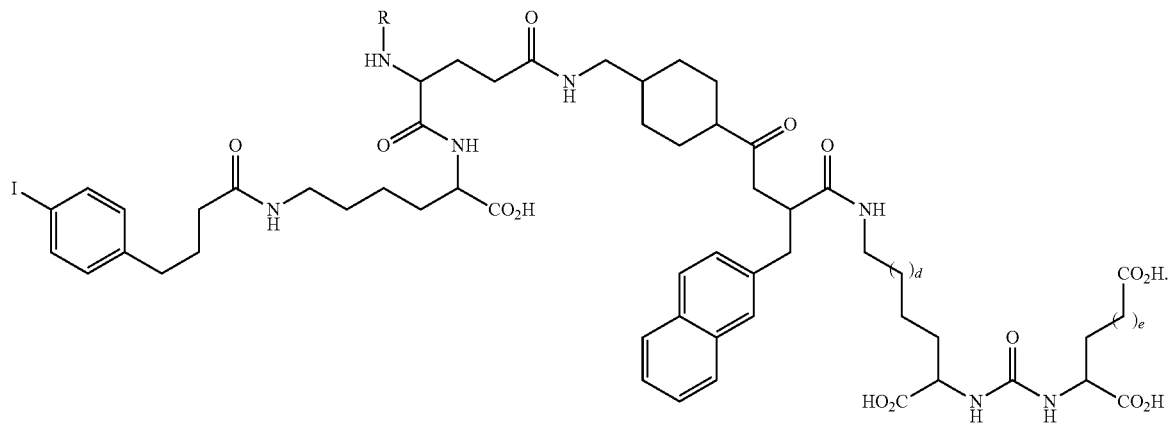
(Ih)

In embodiment I₁₃, the present disclosure provides compounds of Formula (Ii)

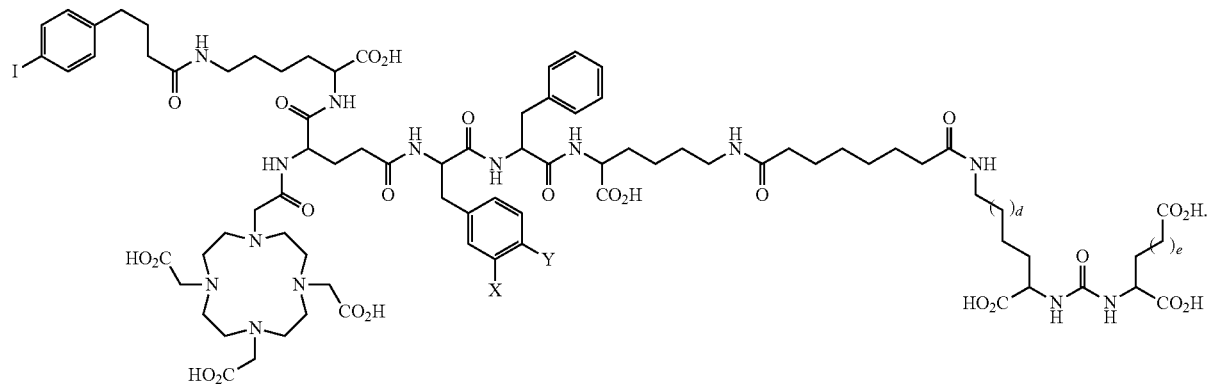

(Ii)

In embodiment I₁₄, the present disclosure provides compounds of Formula (Ij)

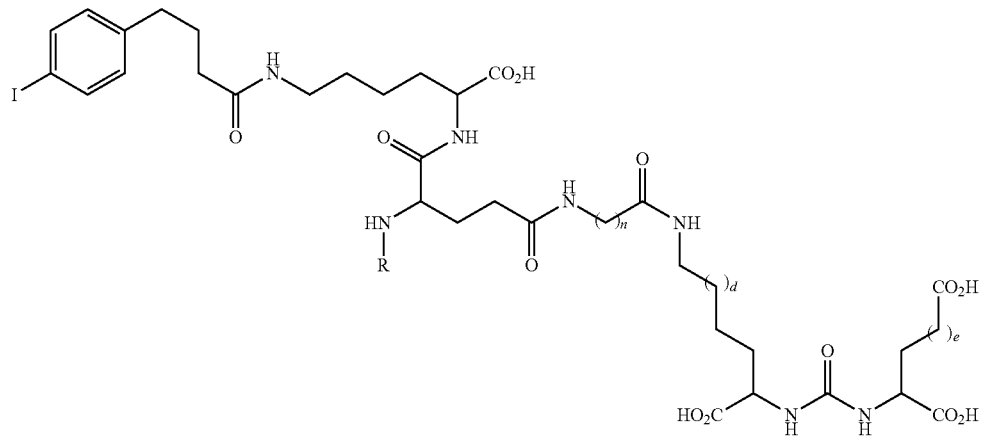

(Ij)

In embodiment I₁₅, the compounds are of any of embodiments I₁-I₁₄, wherein R is a chelating agent optionally chelating a therapeutic radioisotope or a PET-active, SPECT-active, or MRI-active radioisotope. The chelating agent can comprise any chelator known in the art, see, e.g., Parus et al., "Chemistry and bifunctional chelating agents for binding (177)Lu," *Curr Radiopharm.* 2015; 8(2):86-94; Wangler et al., "Chelating agents and their use in radiopharmaceutical sciences," *Mini Rev Med Chem.* 2011 October; 11(11):968-83; Liu, "Bifunctional Coupling Agents for Radiolabeling of Biomolecules and Target-Specific Delivery of Metallic Radionuclides," *Adv Drug Deliv Rev.* 2008 September; 60(12): 1347-1370. Specific examples include, for example:

| Chelator | Structure | R |
|---|---|---|
| DOTA | (DOTA structure) | (DOTA-linked structure) |

-continued

| Chelator | Structure | R |
|---|---|---|
| DOTA-NHS | 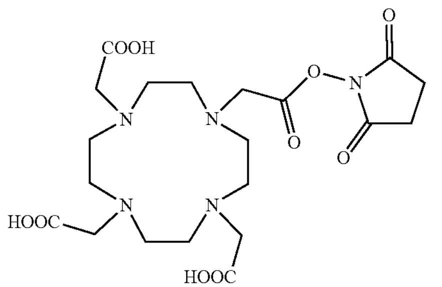 [SMILES: O=C(O)CN1CCN(CC(=O)O)CCN(CC(=O)ON2C(=O)CCC2=O)CCN(CC(=O)O)CC1] | |
| p-SCN-Bn-NOTA | 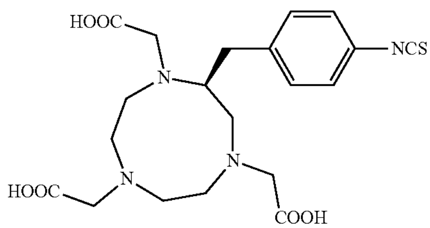 | |
| p-SCN-Bn-PCTA | 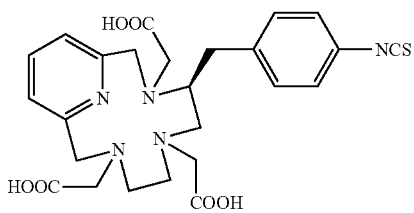 | |
| p-SCN-Bn-Oxo-DO3A | 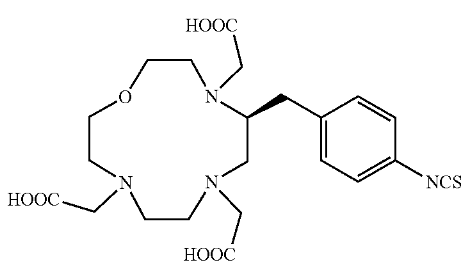 | |
| and desferrioxamine-p-SCN | | |

-continued
| Chelator | Structure | R |
|---|---|---|
| Di-ethylene-triamine-penta-acetic acid (DTPA) | 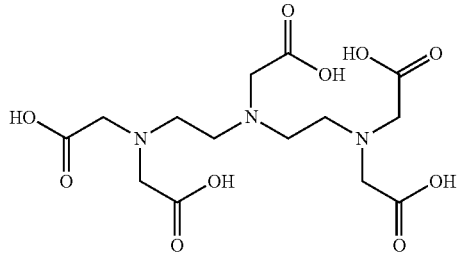 [SMILES: O=C(O)CN(CCN(CC(=O)O)CC(=O)O)CCN(CC(=O)O)CC(=O)O] | 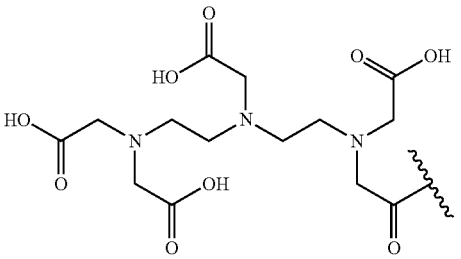 [SMILES: *C(=O)CN(CCN(CCN(CC(=O)O)CC(=O)O)CC(=O)O)CC(=O)O] |
| 1,4,8,11-tetraaza-cyclotetra-decane 1,4,8,11-tetraacetic acid (TETA) | 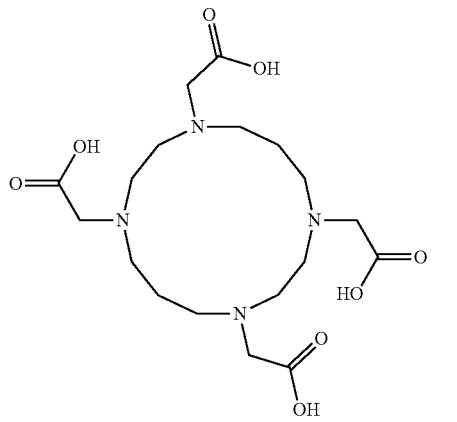 [SMILES: O=C(O)CN1CCCN(CC(=O)O)CCN(CC(=O)O)CCCN(CC(=O)O)CC1] | 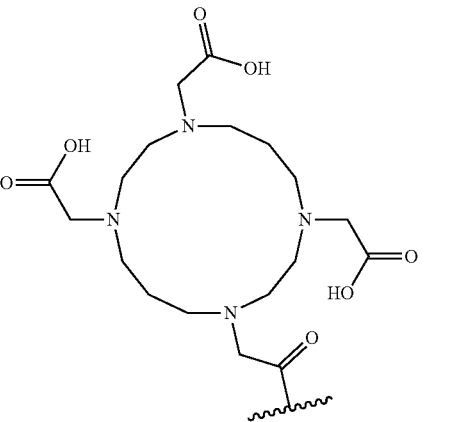 [SMILES: *C(=O)CN1CCCN(CC(=O)O)CCN(CC(=O)O)CCCN(CC(=O)O)CC1] |
| N,N'-Di(2-hydroxy-benzyl)ethylene-diamine-N,N'-diacetic acid (HBED) | 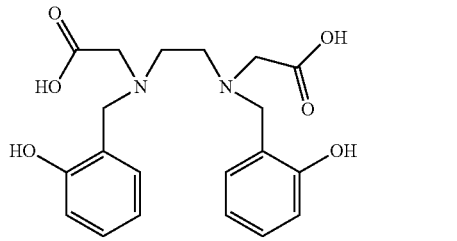 [SMILES: O=C(O)CN(CCN(CC(=O)O)Cc1ccccc1O)Cc1ccccc1O] | 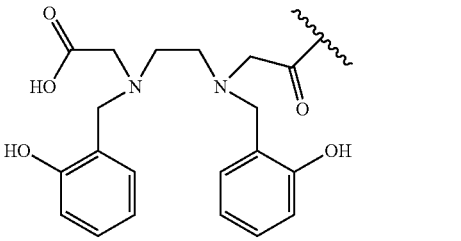 [SMILES: *C(=O)CN(CCN(CC(=O)O)Cc1ccccc1O)Cc1ccccc1O] |
| 4-(4,7-bis(2-(tert-butoxy)-2-oxoethyl)-1,4,7-triaza-cyclo-nonan-1-yl)-5-(tert-butoxy)-5-oxo-pentanoic acid (NODAG) | 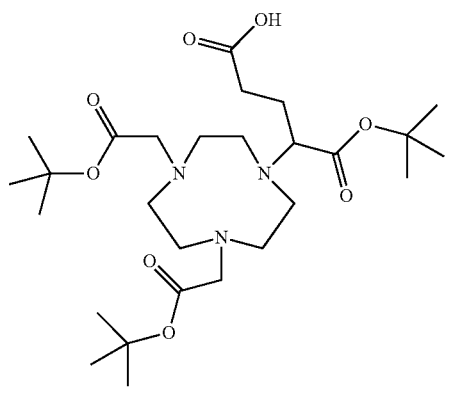 [SMILES: CC(C)(C)OC(=O)CN1CCN(CC(=O)OC(C)(C)C)CCN(C(CCC(=O)O)C(=O)OC(C)(C)C)CC1] | 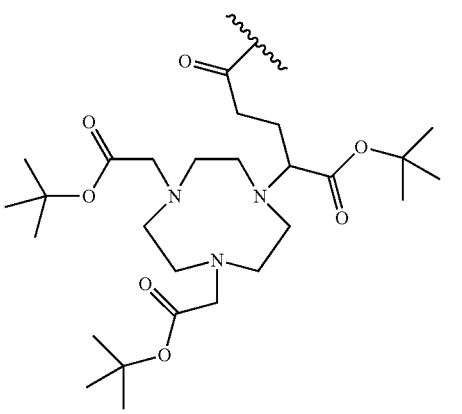 [SMILES: *C(=O)CCC(C(=O)OC(C)(C)C)N1CCN(CC(=O)OC(C)(C)C)CCN(CC(=O)OC(C)(C)C)CC1] |
| 2,2'-(1,4,8,11-tetraaza-bicyclo[6.6.2]hexa-decane-4,11-diyl)diacetic acid (CB-TE2A) | 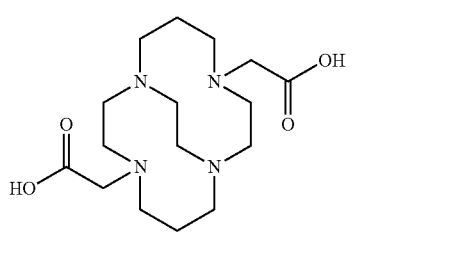 [SMILES: O=C(O)CN1CCCN2CCN(CCCN(CC(=O)O)CC2)CC1] | 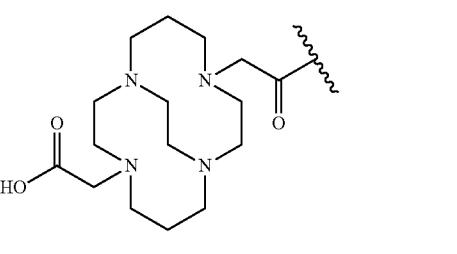 [SMILES: *C(=O)CN1CCCN2CCN(CCCN(CC(=O)O)CC2)CC1] |

| Chelator | Structure | R |
|---|---|---|
| 6-amino-2-(11-(phosphono-methyl)-1,4,8,11-tetraazabicyclo[6.6.2]hexadecan-4-yl)hexanoic acid (CB-TE1K1P) | | |
| HOPO | 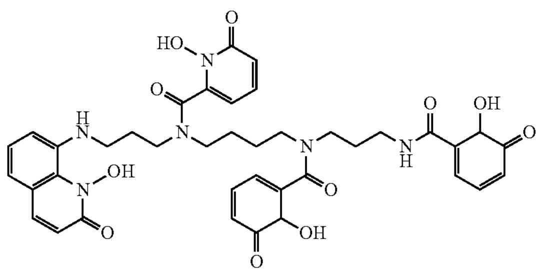 [SMILES: O=C(NCCCN(CCCCN(CCCNc1cccc2ccc(=O)n(O)c12)C(=O)c1cccc(=O)n1O)C(=O)C1=CC=CC(=O)C1O)C1=CC=CC(=O)C1O] | |
| DTPA | 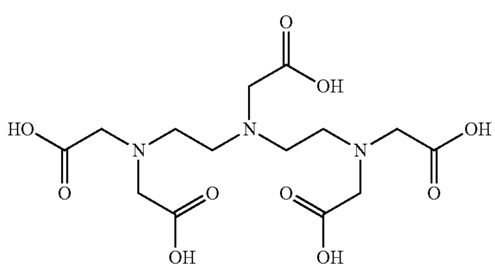 [SMILES: O=C(O)CN(CCN(CC(=O)O)CC(=O)O)CCN(CC(=O)O)CC(=O)O] | |
| EDTA | 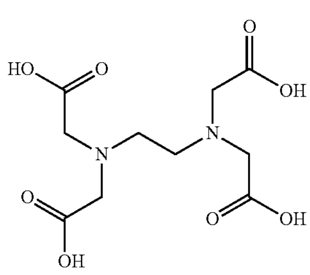 [SMILES: O=C(O)CN(CCN(CC(=O)O)CC(=O)O)CC(=O)O] | |

| Chelator | Structure | R |
|---|---|---|
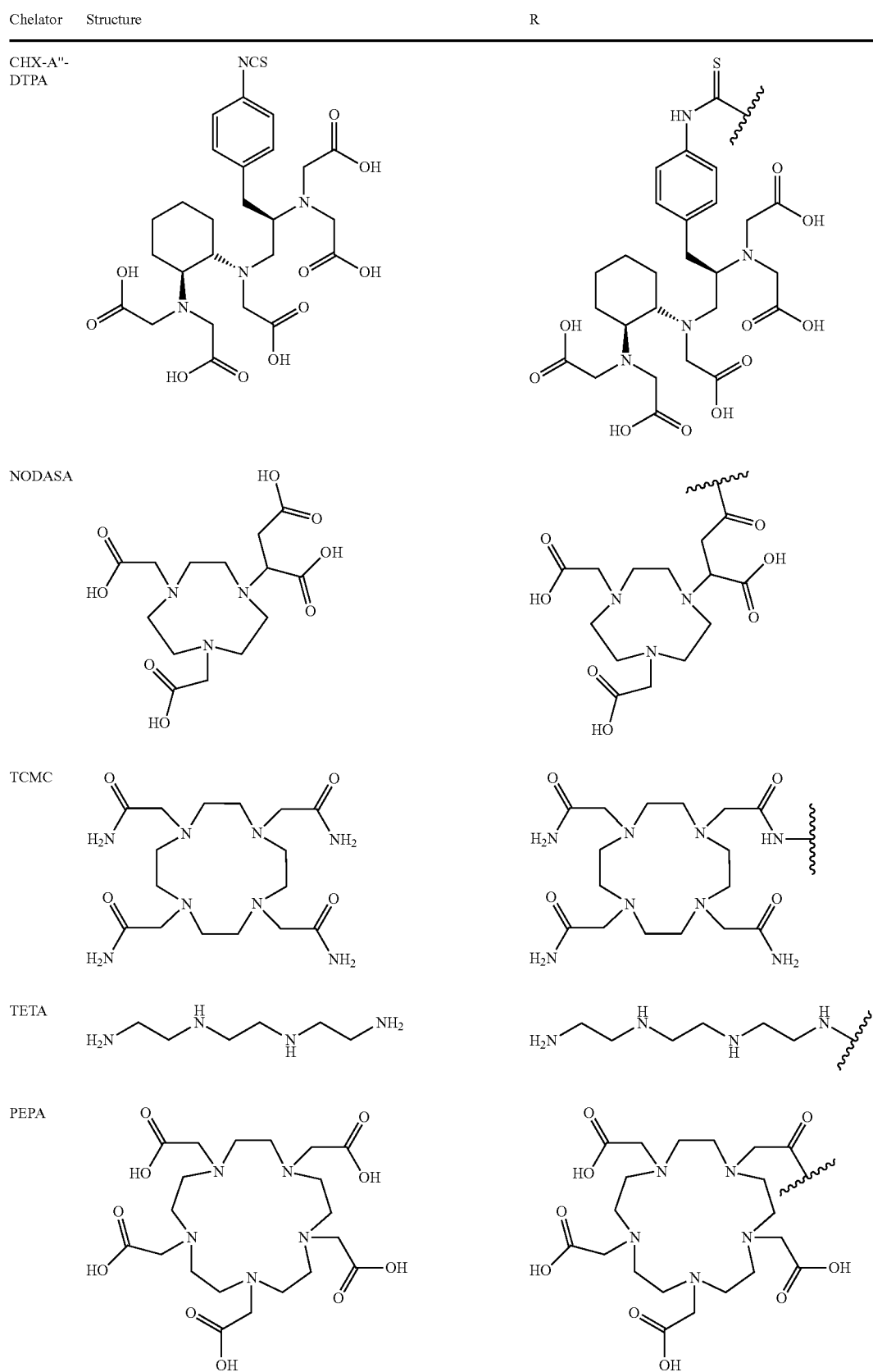
CHX-A''-DTPA
NODASA
TCMC
TETA
PEPA

| Chelator | Structure | R |
|---|---|---|
| HEHA | 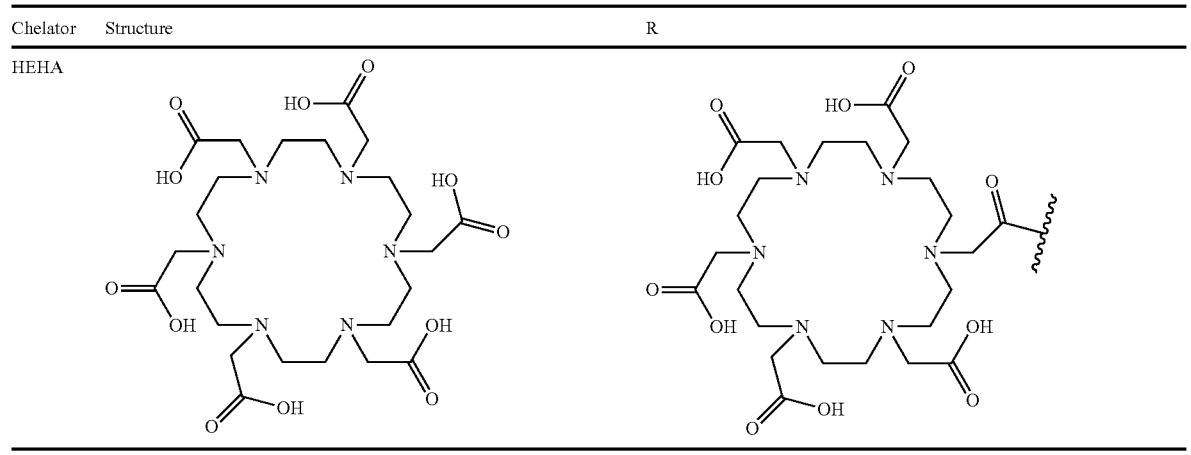 | |
and derivatives thereof.
For example, in embodiment $I_{15a}$, R can be DOTA, bonded through any of its four carboxylic acid groups:
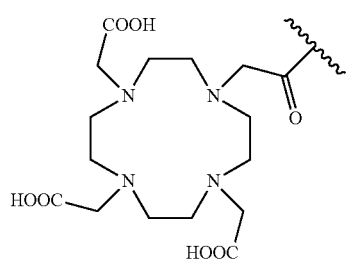
In embodiment $I_{15b}$, R can be
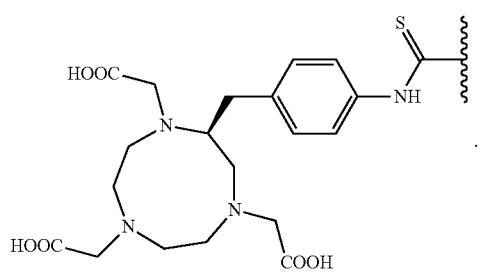 [SMILES: *C(=S)Nc1ccc(C[C@H]2CN(CC(=O)O)CCN(CC(=O)O)CCN2CC(=O)O)cc1]
In embodiment $I_{15c}$, R can be
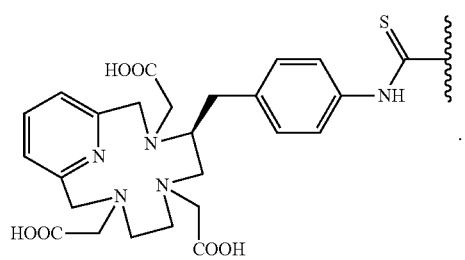 [SMILES: *C(=S)Nc1ccc(C[C@H]2CN(CC(=O)O)CCN(CC(=O)O)Cc3cccc(n3)CN2CC(=O)O)cc1]
In embodiment $I_{15d}$, can be
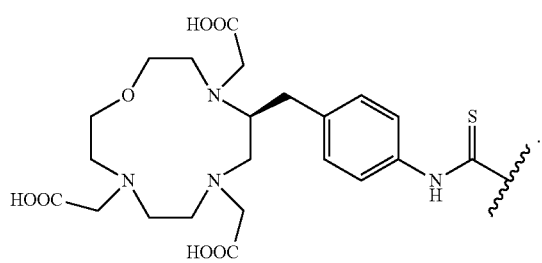 [SMILES: *C(=S)Nc1ccc(C[C@H]2CN(CC(=O)O)CCN(CC(=O)O)CCOCCN2CC(=O)O)cc1]
In embodiment $I_{15e}$, R can be
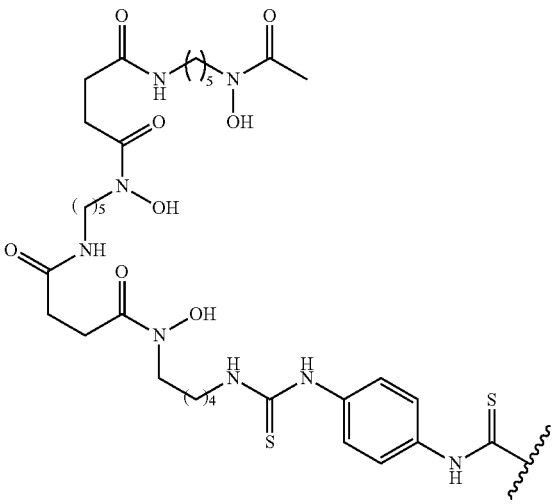

In embodiment I<sub>15f</sub>, R can be
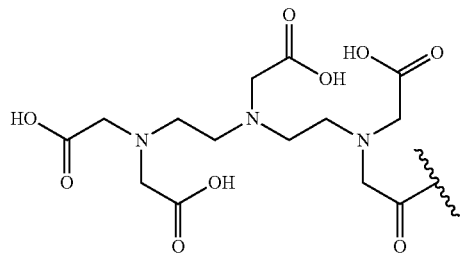
In embodiment I<sub>15g</sub>, R can be
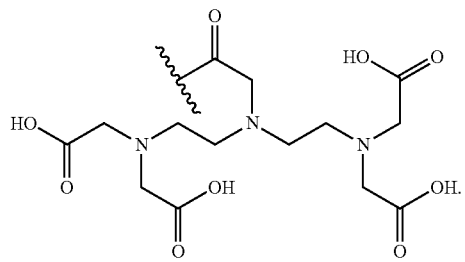 [SMILES: *C(=O)CN(CCN(CC(=O)O)CC(=O)O)CCN(CC(=O)O)CC(=O)O]
In embodiment I<sub>15h</sub>, R can be OH
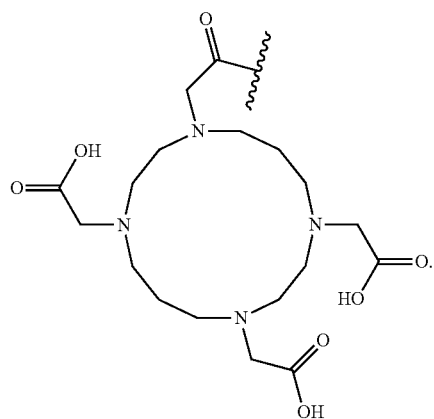 [SMILES: *C(=O)CN1CCCN(CC(=O)O)CCN(CC(=O)O)CCCN(CC(=O)O)CC1]
In embodiment I<sub>15i</sub>, R can be
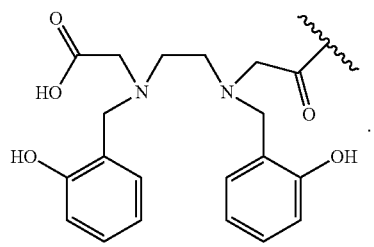 [SMILES: *C(=O)CN(CCN(CC(=O)O)Cc1ccccc1O)Cc1ccccc1O]
In embodiment I<sub>15j</sub>, R can be
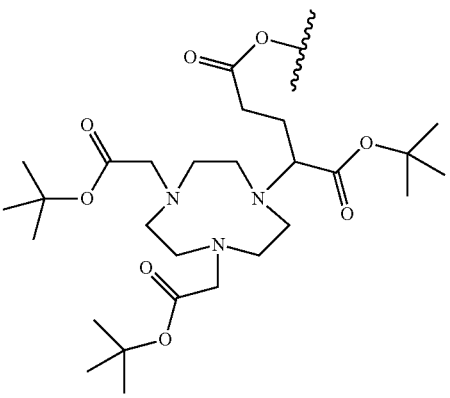
In embodiment I<sub>15k</sub>, R can be
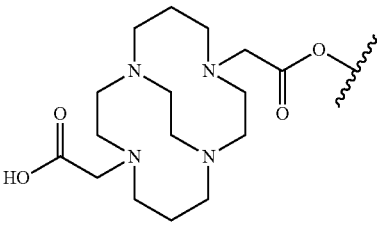
In embodiment I<sub>15l</sub>, R can be
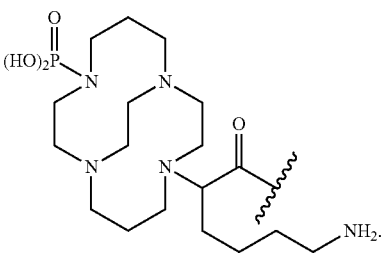

In embodiment $I_{15m}$, R can be
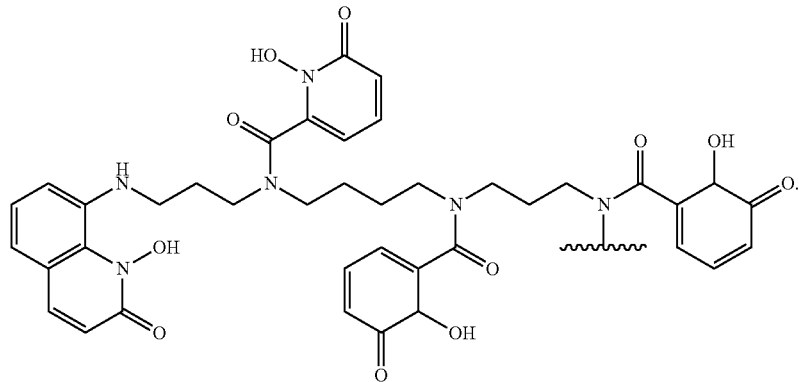 [SMILES: *N(CCCN(CCCCN(CCCNc1cccc2ccc(=O)n(O)c12)C(=O)c1cccc(=O)n1O)C(=O)C1=CC=CC(=O)C1O)C(=O)C1=CC=CC(=O)C1O]
In embodiment $I_{15n}$, R can be
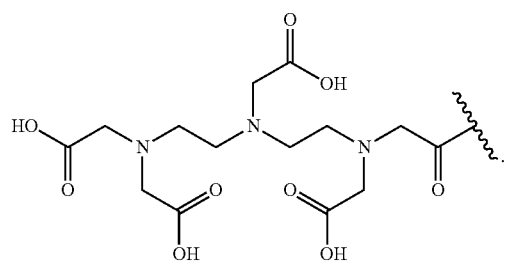 [SMILES: *C(=O)CN(CCN(CCN(CC(=O)O)CC(=O)O)CC(=O)O)CC(=O)O]
In embodiment $I_{15o}$, R can be
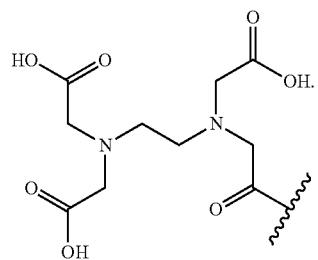
In embodiment $I_{15p}$, R can be
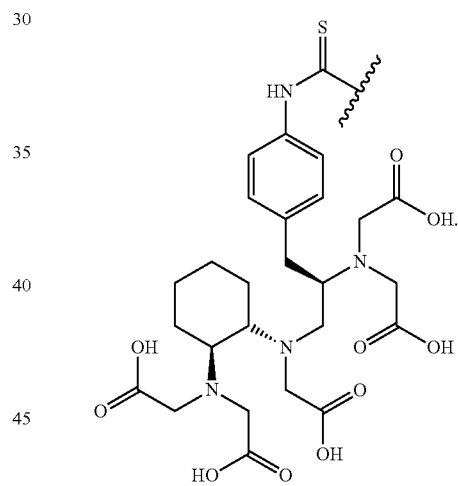
In embodiment $I_{15q}$, R can be
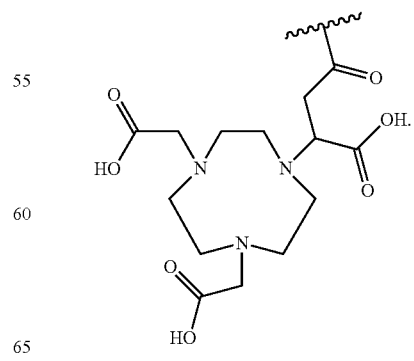

In embodiment $I_{15r}$, R can be

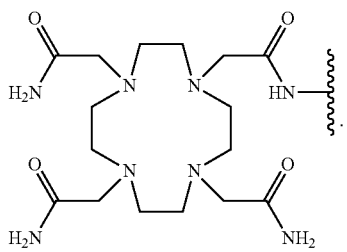

In embodiment $I_{15s}$, R can be

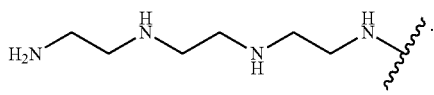

In embodiment $I_{15t}$, R can be

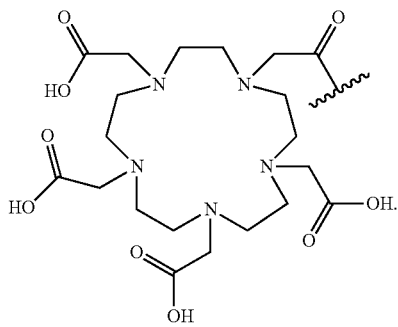 [SMILES: *C(=O)CN1CCN(CC(=O)O)CCN(CC(=O)O)CCN(CC(=O)O)CCN(CC(=O)O)CC1]

In embodiment $I_{15u}$, R can be

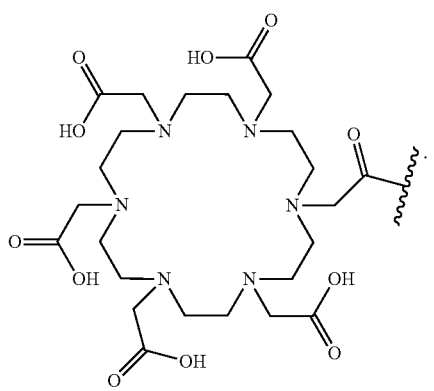 [SMILES: *C(=O)CN1CCN(CC(=O)O)CCN(CC(=O)O)CCN(CC(=O)O)CCN(CC(=O)O)CCN(CC(=O)O)CC1]

If necessary, additional bifunctional chelators can also be readily prepared using literature procedures.

In embodiment $I_{16+}$, each of the preceding compounds may be chelated with a therapeutic radioisotope or a PET-active, SPECT-active, or MRI-active radioisotope selected from $^{66}$Ga, $^{68}$Ga, $^{64}$Cu, $^{89}$Zr, $^{186/188}$Re, $^{89}$Y, $^{90}$Y, $^{177}$Lu, $^{153}$Sm, $^{212}$Bi, $^{213}$Bi, $^{225}$Ac, $^{227}$Th, $^{111}$In, $^{212}$Pb and $^{223}$Ra.

In embodiment $I_{16}$, each of the preceding compounds may be chelated with a therapeutic radioisotope or a PET-active, SPECT-active, or MRI-active radioisotope selected from $^{68}$Ga, $^{64}$Cu, $^{89}$Zr, $^{186/188}$Re, $^{90}$Y, $^{177}$Lu $^{153}$Sm, $^{213}$Bi, $^{225}$Ac, $^{227}$Th, and $^{223}$Ra.

In embodiment $I_{16a}$, each of the preceding compounds may be chelated with a therapeutic radioisotope or a PET-active, SPECT-active, or MRI-active radioisotope that is $^{89}$Zr.

In embodiment $I_{16b}$, each of the preceding compounds may be chelated with a therapeutic radioisotope or a PET-active, SPECT-active, or MRI-active radioisotope that is $^{64}$Cu.

In embodiment $I_{16c}$, each of the preceding compounds may be chelated with a therapeutic radioisotope or a PET-active, SPECT-active, or MRI-active radioisotope that is with $^{68}$Ga.

In embodiment $I_{16d}$, each of the preceding compounds may be chelated with a therapeutic radioisotope or a PET-active, SPECT-active, or MRI-active radioisotope that is $^{186/188}$Re.

In embodiment $I_{16e}$, each of the preceding compounds may be chelated with a therapeutic radioisotope or a PET-active, SPECT-active, or MRI-active radioisotope that is $^{90}$Y.

In embodiment $I_{16f}$, each of the preceding compounds may be chelated with a therapeutic radioisotope or a PET-active, SPECT-active, or MRI-active radioisotope that is $^{177}$Lu.

In embodiment $I_{16g}$, each of the preceding compounds may be chelated with a therapeutic radioisotope or a PET-active, SPECT-active, or MRI-active radioisotope that is $^{153}$Sm.

In embodiment $I_{16h}$, each of the preceding compounds may be chelated with a therapeutic radioisotope or a PET-active, SPECT-active, or MRI-active radioisotope that is $^{213}$Bi.

In embodiment $I_{16i}$, each of the preceding compounds may be chelated with a therapeutic radioisotope or a PET-active, SPECT-active, or MRI-active radioisotope that is $^{225}$Ac.

In embodiment $I_{16j}$, each of the preceding compounds may be chelated with a therapeutic radioisotope or a PET-active, SPECT-active, or MRI-active radioisotope that is $^{227}$Th.

In embodiment $I_{16k}$, each of the preceding compounds may be chelated with a therapeutic radioisotope or a PET-active, SPECT-active, or MRI-active radioisotope that is $^{223}$Ra.

In embodiment $I_{16l}$, each of the preceding compounds may be chelated with a therapeutic radioisotope or a PET-active, SPECT-active, or MRI-active radioisotope that is $^{66}$Ga.

In embodiment $I_{16m}$, each of the preceding compounds may be chelated with a therapeutic radioisotope or a PET-active, SPECT-active, or MRI-active radioisotope that is $^{89}$Y.

In embodiment $I_{16n}$, each of the preceding compounds may be chelated with a therapeutic radioisotope or a PET-active, SPECT-active, or MRI-active radioisotope that is $^{212}$Bi.

In embodiment $I_{16o}$, each of the preceding compounds may be chelated with a therapeutic radioisotope or a PET-active, SPECT-active, or MRI-active radioisotope that is $^{111}$In.

In embodiment $I_{16p}$, each of the preceding compounds may be chelated with a therapeutic radioisotope or a PET-active, SPECT-active, or MRI-active radioisotope that is, $^{212}$Pb.

In embodiment I₁₇, the compounds are of any of embodiments I₁-I₁₆ⱼ, wherein R¹ and R² are each independently selected from one of groups (5a)-(5o):
- (5a) hydrogen, C₁-C₆ alkyl or a protecting group.
- (5b) hydrogen or C₁-C₆ alkyl.
- (5c) C₁-C₆ alkyl or a protecting group.
- (5d) C₁-C₆ alkyl
- (5e) hydrogen or a protecting group.
- (5f) hydrogen.
- (5g) a protecting group
- (5h) Any of groups (5a)-(5d), where C₁-C₆alkyl is methyl, ethyl, n-propyl, iso-propyl, n-butyl, sec-butyl, tert-butyl, n-pentyl or n-hexyl.
- (5i) Any of groups (5a)-(5d), where C₁-C₆alkyl is methyl, ethyl, n-propyl, iso-propyl, n-butyl, sec-butyl or tert-butyl.
- (5j) Any of groups (5a)-(5d), where C₁-C₆alkyl is methyl, ethyl, n-propyl or tert-butyl.
- (5k) Any of groups (5a)-(5d), where C₁-C₆alkyl is methyl, ethyl or tert-butyl.
- (5l) Any of groups (5a)-(5d), where C₁-C₆alkyl is methyl or ethyl.
- (5m) Any of groups (5a)-(5d), where C₁-C₆alkyl is methyl.
- (5n) Any of groups (5a)-(5d), where C₁-C₆alkyl is ethyl.
- (5o) Any of groups (5a)-(5g), where C₁-C₆alkyl is tert-butyl.

A "protecting group" as used herein include, but are not limited to, optionally substituted benzyl, t-butyl ester, allyl ester, alkyl esters (e.g., methyl, ethyl, propyl, butyl), fluorenylmethoxycarbonyl groups (Fmoc), and amino, carboxylic acid and phosphorus acid protecting groups described in Greene's Protective Groups in Organic Synthesis, 4th Edition (which is incorporated by reference). In some embodiments, R¹ is a carboxylic acid protecting group (e.g., a methyl or t-butyl ester). In some embodiments, R² is a nitrogen protecting group (e.g., Boc, or benzyl).

Optionally benzyl groups include, but are not limited to, unsubstituted benzyl, triphenylmethyl (trityl), diphenylmethyl, o-nitrobenzyl, 2,4,6-trimethylbenzyl, p-bromobenzyl, p-nitrobenzyl, p-methoxybenzyl (PMB), 2,6-dimethoxybenzyl, 4-(methylsulfinyl)benzyl, 4-sulfobenzyl, 4-azidomethoxybenzyl, and piperonyl, and benzyl protecting groups for carboxylic and phosphorus acids disclosed in Greene's Protective Groups in Organic Synthesis (the relevant parts of which are incorporated by reference).

In embodiment I₁₈, the compound of Formula (I) may be selected from the following:

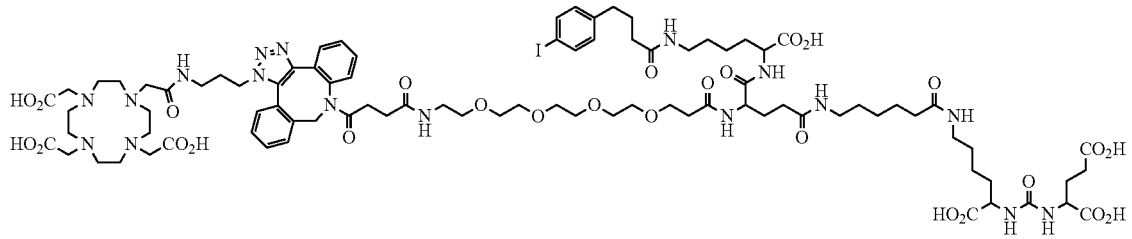

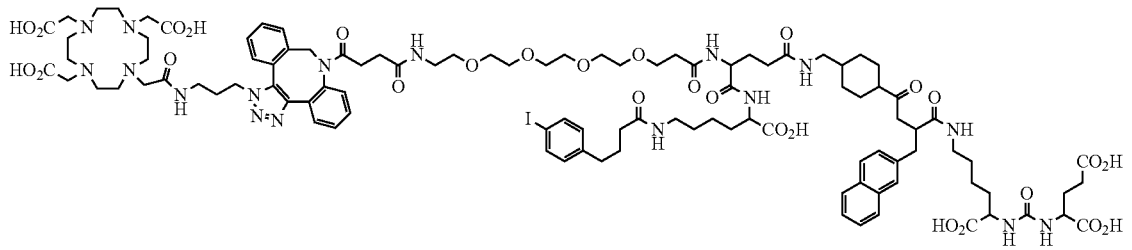

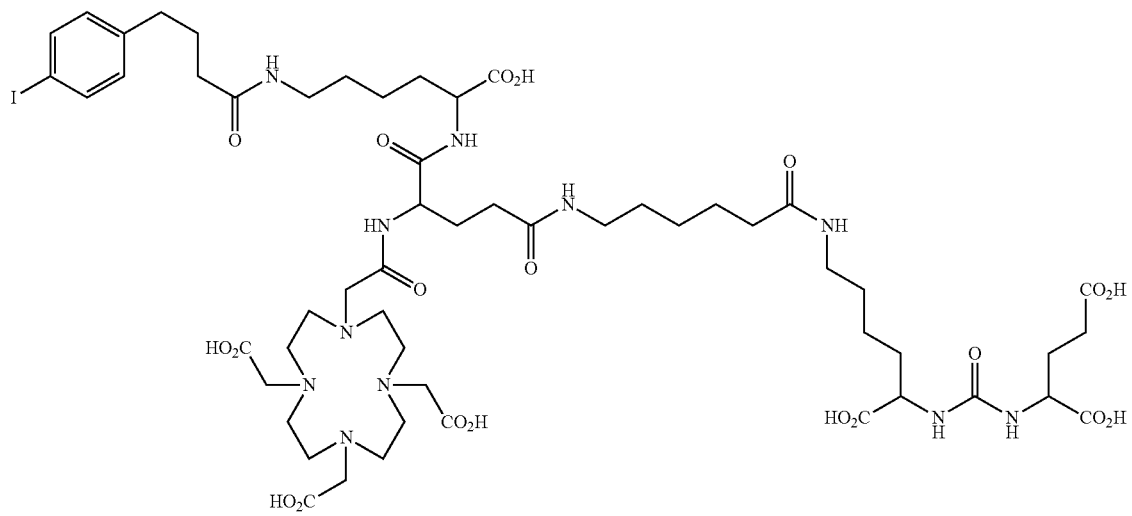 [SMILES: O=C(O)CCC(NC(=O)NC(CCCCNC(=O)CCCCCNC(=O)CCC(NC(=O)CN1CCN(CC(=O)O)CCN(CC(=O)O)CCN(CC(=O)O)CC1)C(=O)NC(CCCCNC(=O)CCCc1ccc(I)cc1)C(=O)O)C(=O)O)C(=O)O]

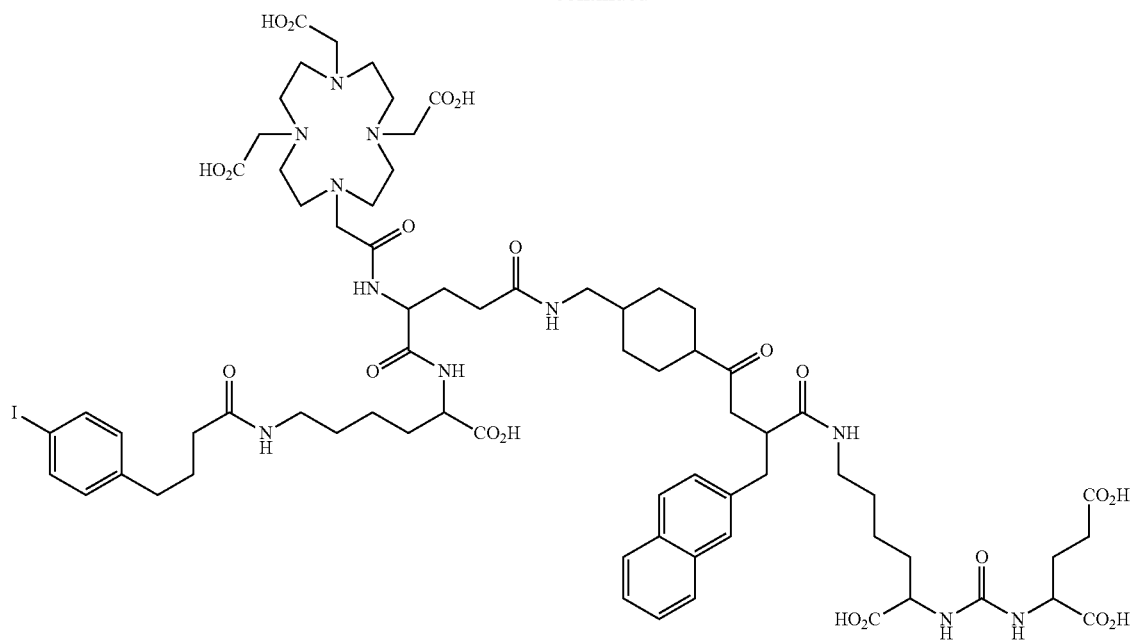 [SMILES: O=C(O)CCC(NC(=O)NC(CCCCNC(=O)C(CC(=O)C1CCC(CNC(=O)CCC(NC(=O)CN2CCN(CC(=O)O)CCN(CC(=O)O)CCN(CC(=O)O)CC2)C(=O)NC(CCCCNC(=O)CCCc2ccc(I)cc2)C(=O)O)CC1)Cc1ccc2ccccc2c1)C(=O)O)C(=O)O]
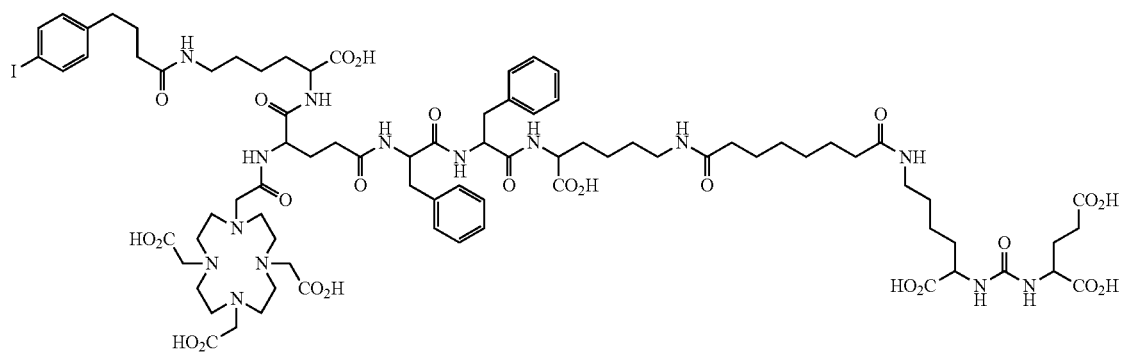
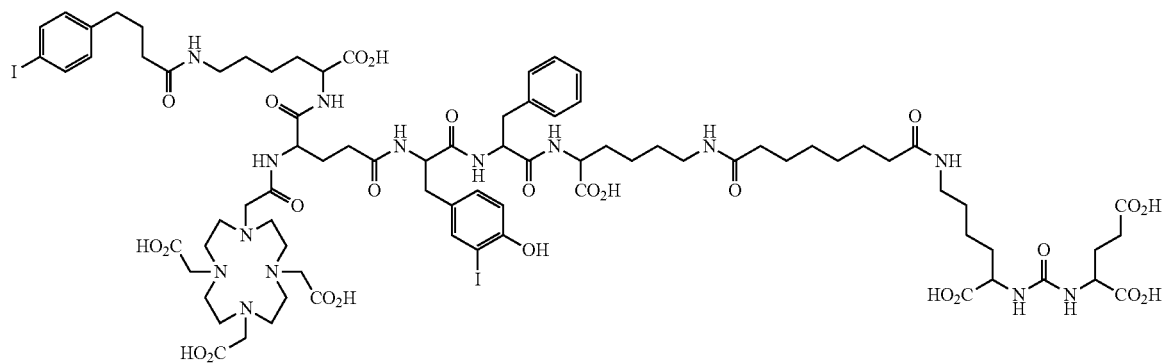

-continued

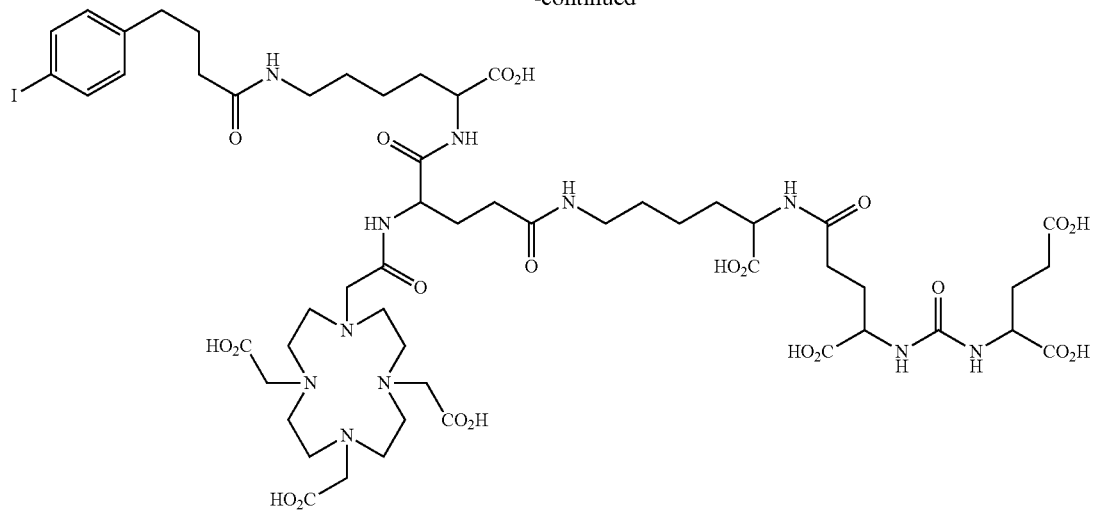

or a pharmaceutically acceptable salt thereof.

In embodiment 119, the present disclosure provides a pharmaceutical composition comprising a compound of Formula (I) and a pharmaceutically acceptable carrier.

In embodiment 120, the present disclosure provides a method for imaging one or more prostate cancer cells in a patient comprising administering to the patient a compound of Formula (I) or a pharmaceutical composition thereof. The method may further include imaging the compound of Formula (I) in vivo. The imaging can be performed with any PET-imaging techniques known in the art.

In embodiment $II_1$ of this aspect, the disclosure provides compounds of Formula (II)

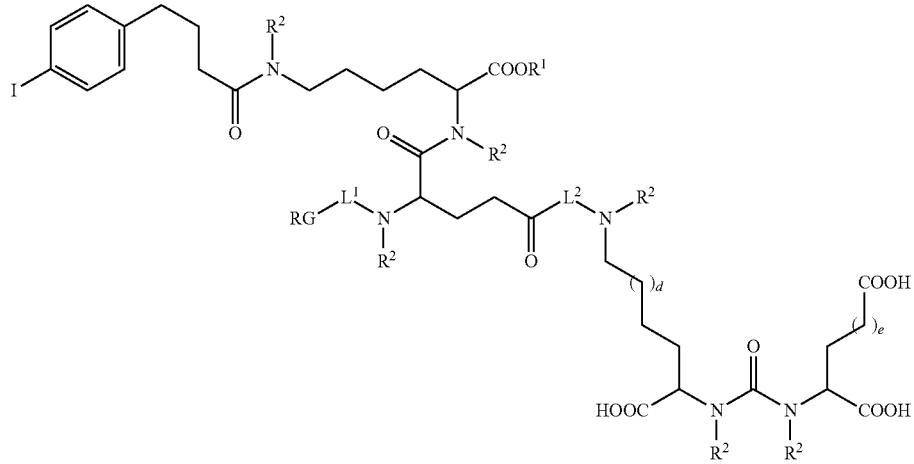

or a pharmaceutically acceptable salt thereof, wherein
$L^1$ and $L^2$ are each independently a covalent bond or a divalent linking group;
d and e are each independently 0, 1, 2, 3, 4 or 5;
RG is —NH$_2$ or

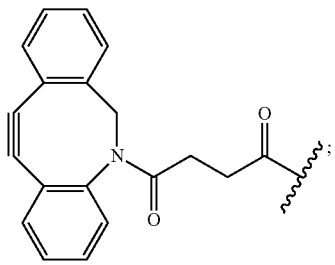 [SMILES: *C(=O)CCC(=O)N1Cc2ccccc2C#Cc2ccccc21]

and
each $R^1$ and $R^2$ are each independently hydrogen, $C_1$-$C_6$ alkyl or a protecting group.

In embodiment II$_{1a}$, RG is —NH$_2$.
In embodiment II$_{1b}$, RG is

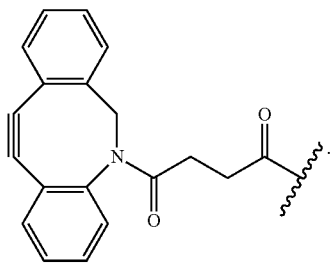 [SMILES: *C(=O)CCC(=O)N1Cc2ccccc2C#Cc2ccccc21]

In embodiment II$_2$, the compound is of embodiment II$_1$, wherein RG-L$^1$- is of the formula L$^{RG}$-NH—CH$_2$CH$_2$—(OCH$_2$CH$_2$-)$_y$—C(O)—, wherein
y is 1, 2, 3, 4, 5, 6, 7, 8, 9, 10, 11 or 12; and
L$^{RG}$ is

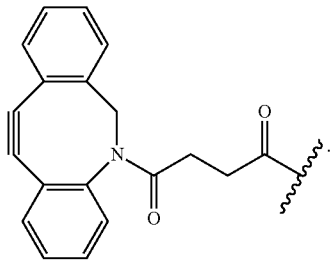 [SMILES: *C(=O)CCC(=O)N1Cc2ccccc2C#Cc2ccccc21]

In embodiment II$_3$, y in embodiment II$_1$-II$_{1b}$ or II$_2$ is selected from one of groups (1a)-(1x).

In another aspect, the disclosure provides a method for preparing a compound according to Formula (I). Compounds according to the invention can be made using art recognized techniques combined with methods analogous to those disclosed below.

Definitions

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" PSMA with a compound includes the administration of a compound described herein to an individual or patient, such as a human, as well as, for example, introducing a compound into a sample containing a cellular or purified preparation containing PSMA.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—(CH$_2$)$_n$—COOH where n is 0-4, and the like. Non-toxic pharmaceutical base addition salts include salts of bases such as sodium, potassium, calcium, ammonium, and the like. In certain embodiments, the pharmaceutically acceptable salt is a sodium salt. Those skilled in the art will recognize a wide variety of non-toxic pharmaceutically acceptable addition salts.

Pharmaceutical compositions suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Compositions can be administered, for example, by intravenous infusion, orally, topically, intraperitoneally, intravesically or intrathecally.

The term "alkyl" as used herein, means a straight or branched chain hydrocarbon containing from 1 to 10 carbon atoms, unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —CH$_2$—, —CH$_2$CH$_2$—, —CH$_2$CH$_2$CHC(CH$_3$)—, —CH$_2$CH(CH$_2$CH$_3$)CH$_2$—.

The term "heterocyclyl" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are each independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are each independently oxo or thia.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "thia" as used herein means a =S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

EXAMPLES

Example 1: Example Synthesis

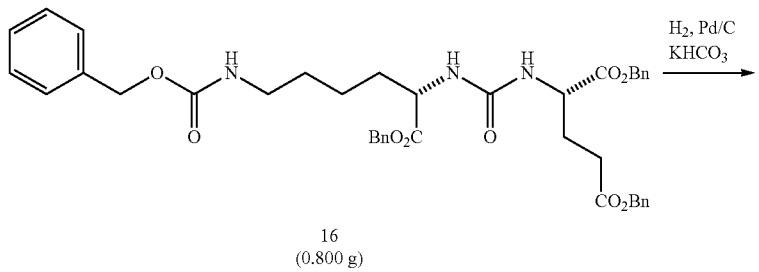

16
(0.800 g)

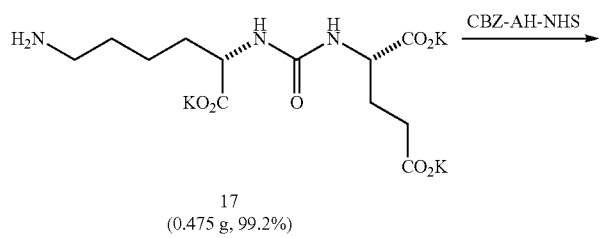

17
(0.475 g, 99.2%)

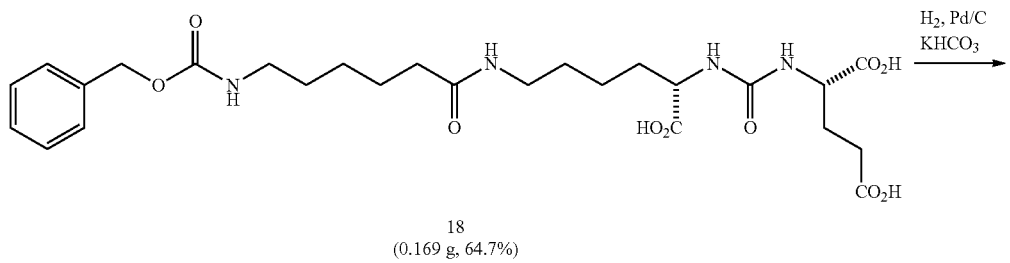

18
(0.169 g, 64.7%)

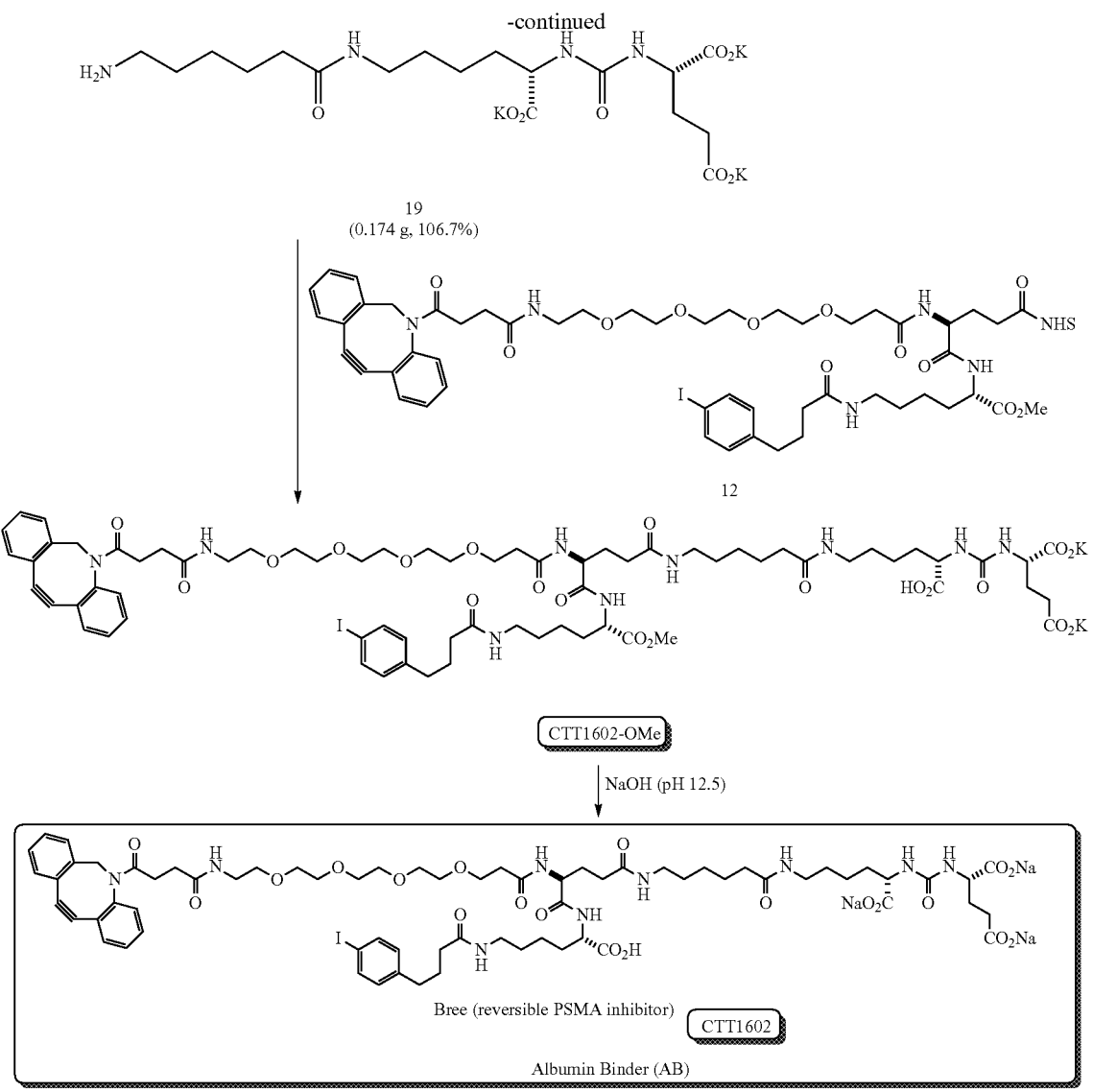

We claim:

1. A compound of Formula (I)

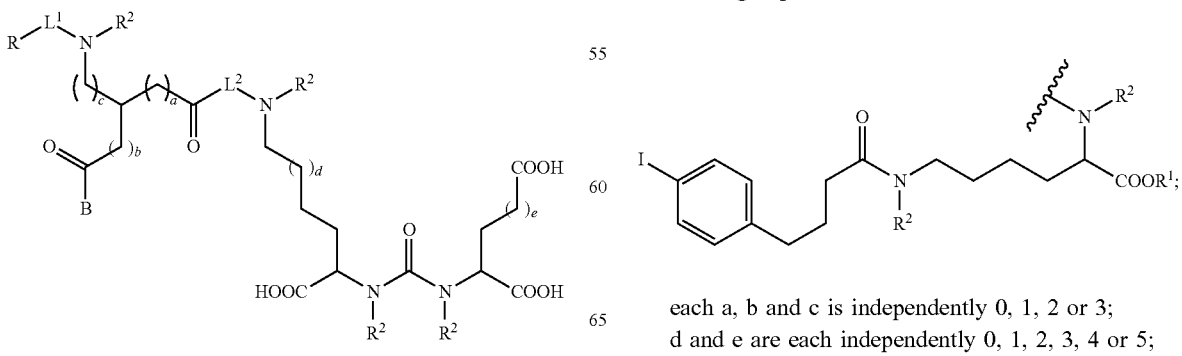

or a pharmaceutically acceptable salt thereof, wherein
  $L^1$ and $L^2$ are each independently a covalent bond or a divalent linking group;
  R is a chelating agent optionally chelating a therapeutic radioisotope or a PET-active, SPECT-active, or MRI-active radioisotope, or R is a therapeutic drug;
  B is a group of the formula each a, b and c is independently 0, 1, 2 or 3;
d and e are each independently 0, 1, 2, 3, 4 or 5;
$R^1$ is hydrogen, $C_1$-$C_6$ alkyl or a protecting group; and each R² is independently hydrogen, C₁-C₆ alkyl or a protecting group.

2. A compound or pharmaceutically acceptable salt thereof according to claim 1 which has Formula (Ia)

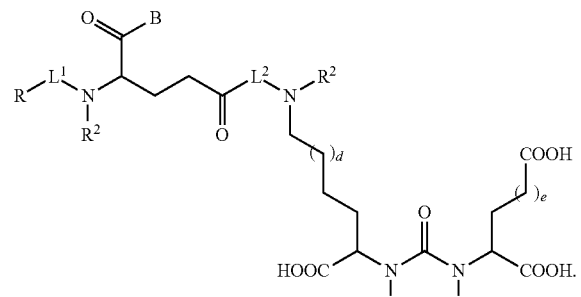
(Ia)

3. A compound or pharmaceutically acceptable salt thereof according to claim 1, which has Formula (Ic)

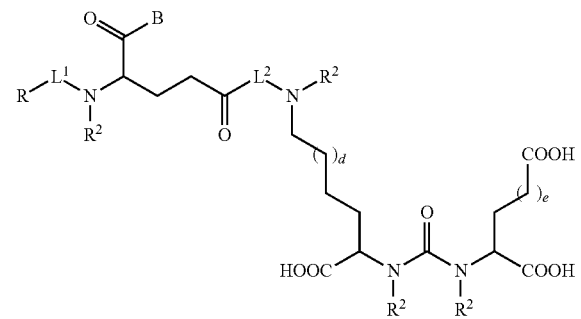
(Ic)

4. The compound of claim 1, wherein L¹ is

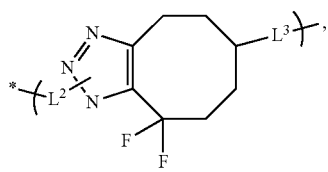

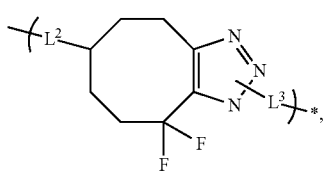

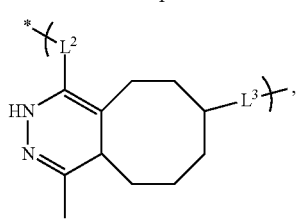

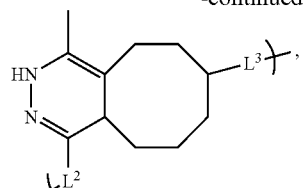

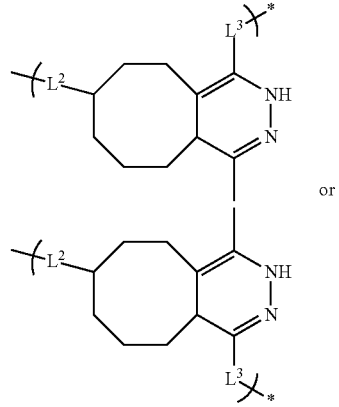

wherein
L² is —(CH₂)ₜN(H)—*, wherein t is 1 to 30; and
L³ is #—(CH₂)ᵤ—C(O)—, #—(CH₂)ᵤ—Z—Y—C(O)—, #—C(O)—(CH₂)ᵤ—C(O)— or #—C(O)—(CH₂)ᵤ—Z—Y—C(O)—, wherein
the # end of L³ is attached to the dibenzocyclooctyne or triazolyl group above,
Y is —(CH₂)ᵤ— or —CH₂CH₂—(OCH₂CH₂)ₙ—, wherein n is 1-20 (e.g., 4-12, or 4, or 8, or 12), and wherein the -end is attached to Z;
u is 1 to 30; and
Z is —C(O)O—, —C(O)N(R⁰⁰)—, —OC(O)—, —N(R⁰⁰)C(O)—, —S(O)₂N(R⁰⁰)—, —N(R⁰⁰)S(O)₂—, —OC(O)O—, —OC(O)N(R⁰⁰)—, —N(R⁰⁰)C(O)O—, or —N(R⁰⁰))C(O)N(R⁰⁰)—, wherein each R⁰⁰ is independently hydrogen or C₁-C₆ alkyl.

5. The compound of claim 1, wherein
L² is a group of the formula

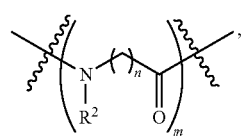

wherein
m is 1, 2, 3, or 4;
each n is independently 1, 2, 3, 4, 5, 6, 7, 8, 9, 10, 11 or 12;
provided that m·(n+2) is greater than or equal to 3 and less than or equal to 21;
or a group of the formula

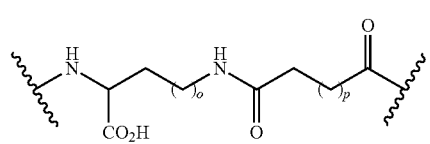

wherein o and p are each independently 0, 1, 2, 3, 4, 5, 6, 7, 8, 9, 10, 11 or 12;
or a group of the formula
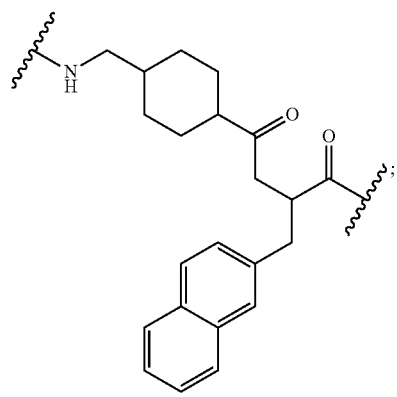 [SMILES: *NCC1CCC(C(=O)CC(Cc2ccc3ccccc3c2)C(*)=O)CC1]
or a group of the formula
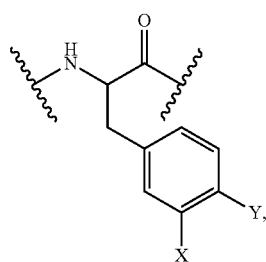
wherein X and Y are each independently hydrogen, halogen, hydroxy or alkoxy;
or a combination thereof.
6. A compound according to claim 1, which has Formula (Ie)
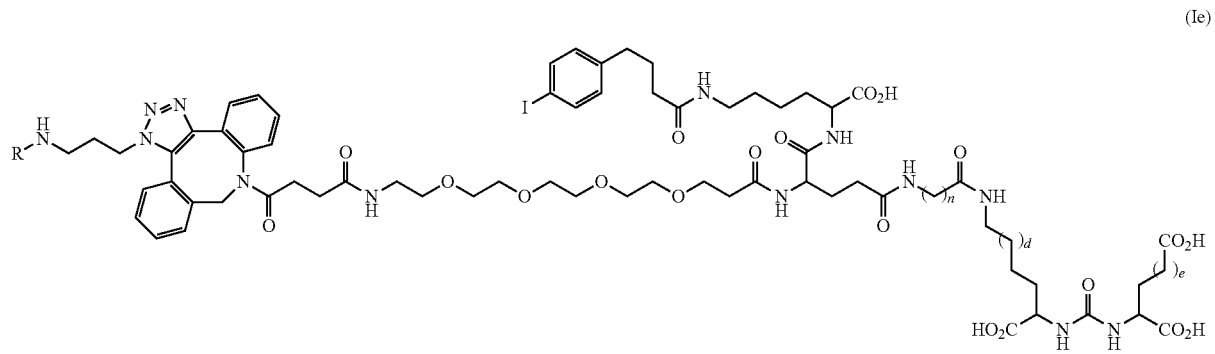
wherein n is 1, 2, 3, 4, 5, 6 or 7.

7. A compound according to claim 1, which has Formula (If)
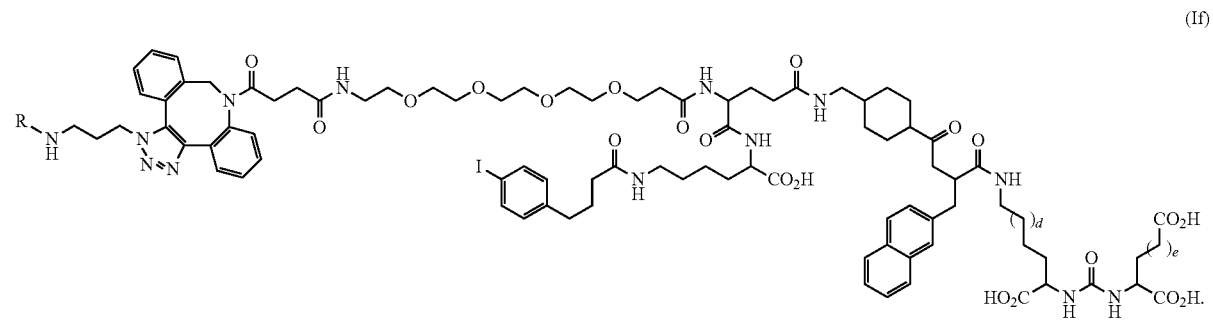
8. A compound according to claim 1, which has Formula (Ig)
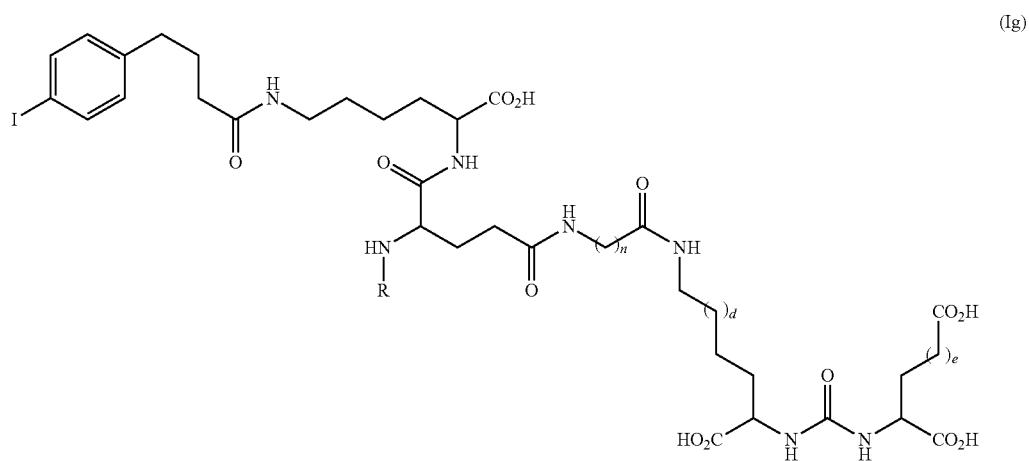
wherein n is 1, 2, 3, 4, 5, 6 or 7.
9. A compound according to claim 1, which has Formula (Ih)
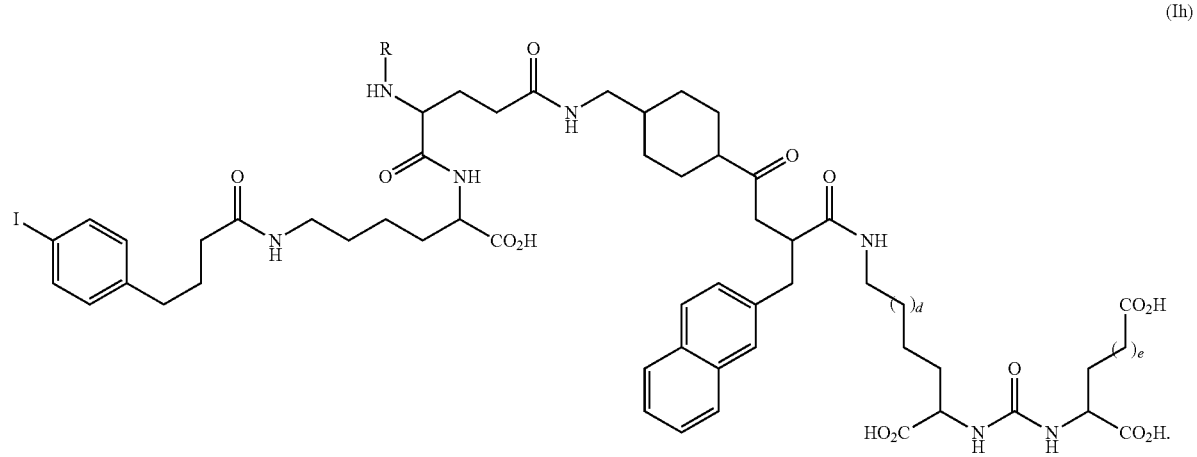

10. A compound according to claim 1, which has Formula (Ii)

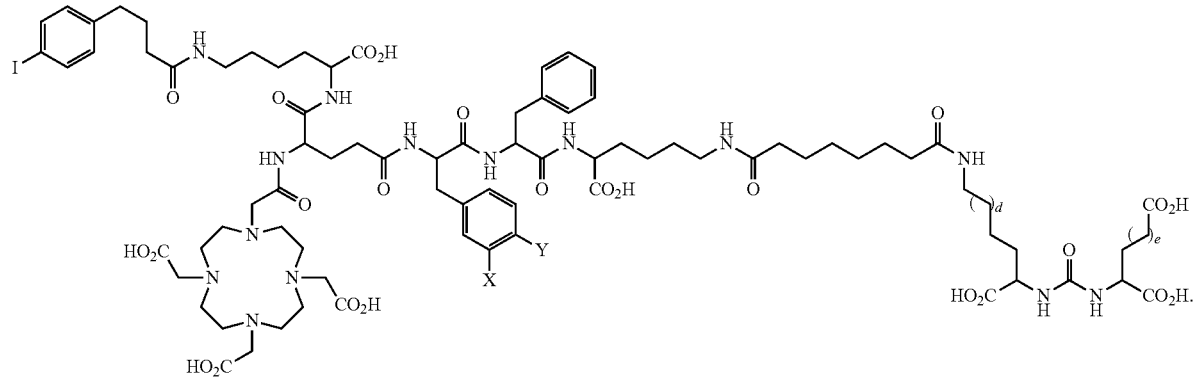

11. A compound according to claim 1, which has Formula (Ij)

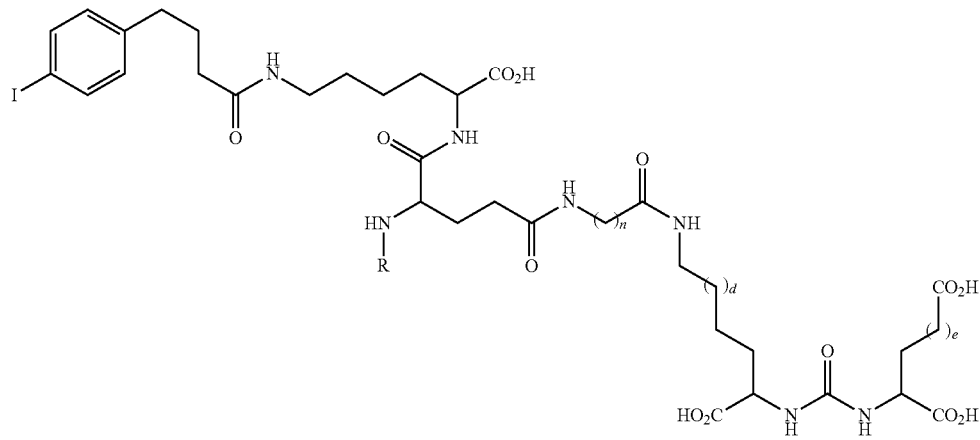

wherein n is 1, 2, 3, 4, 5, 6 or 7.

12. A compound according to claim 1, wherein R comprises DOTA, NOTA, PCTA, DO3A, or desferrioxamine.

13. A compound according to claim 1, wherein the chelating agent is chelating a therapeutic radioisotope or a PET-active, SPECT-active, or MRI-active radioisotope that is $^{66}$Ga, $^{68}$Ga, $^{64}$Cu, $^{89}$Zr, $^{186/188}$Re, $^{89}$Y, $^{90}$Y, $^{177}$Lu, $^{153}$Sm, $^{212}$Bi, $^{213}$Bi, $^{225}$Ac, $^{227}$Th, $^{111}$In, $^{212}$Pb and $^{223}$Ra.

14. The compound of claim 1, wherein each $R^1$ is hydrogen.

15. The compound of claim 1, wherein each $R^2$ is hydrogen.

16. A compound according to claim 1 that is

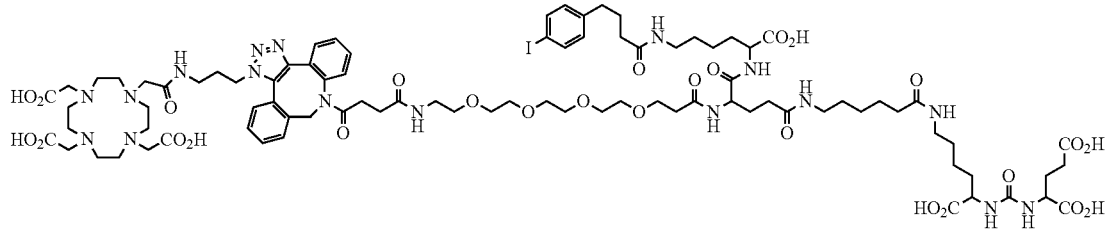

-continued
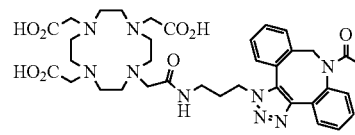
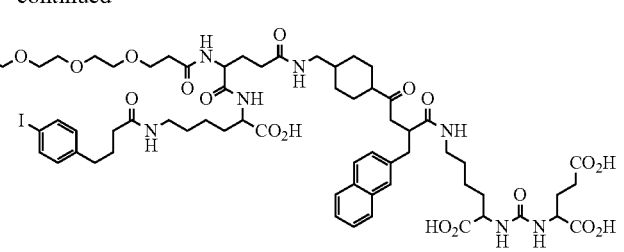
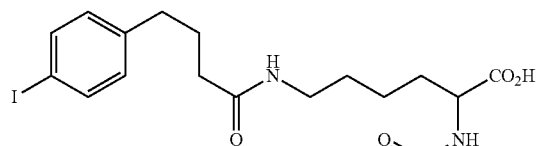
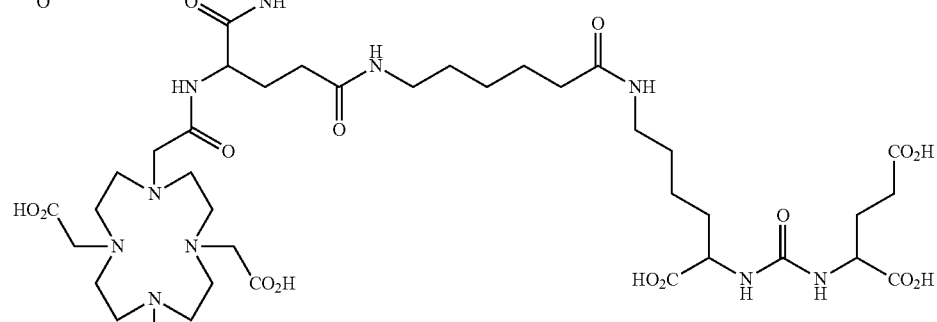
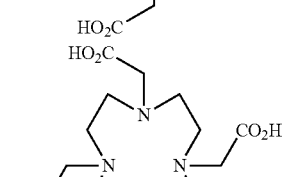
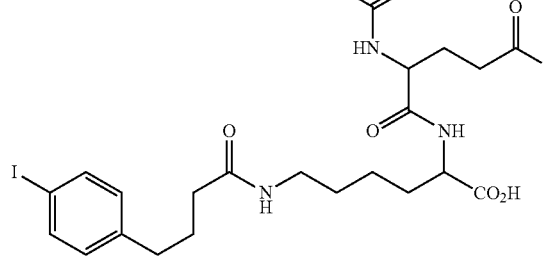
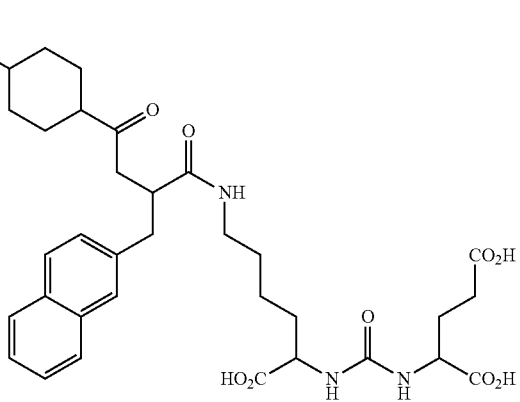
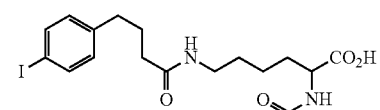
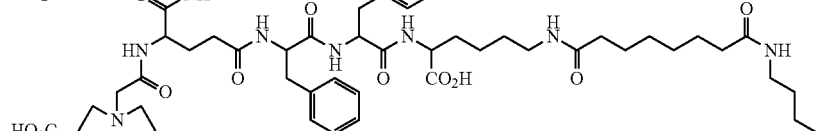
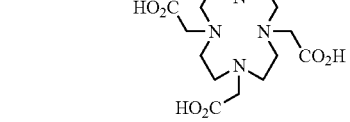
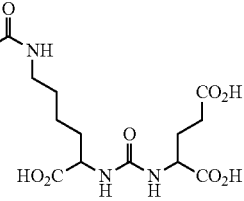

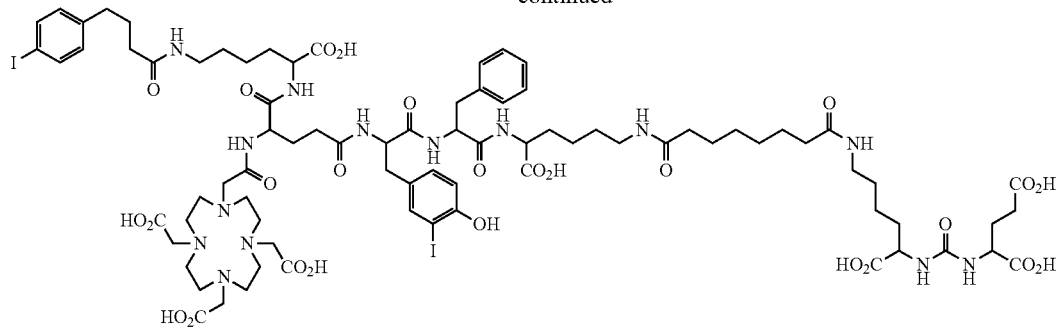

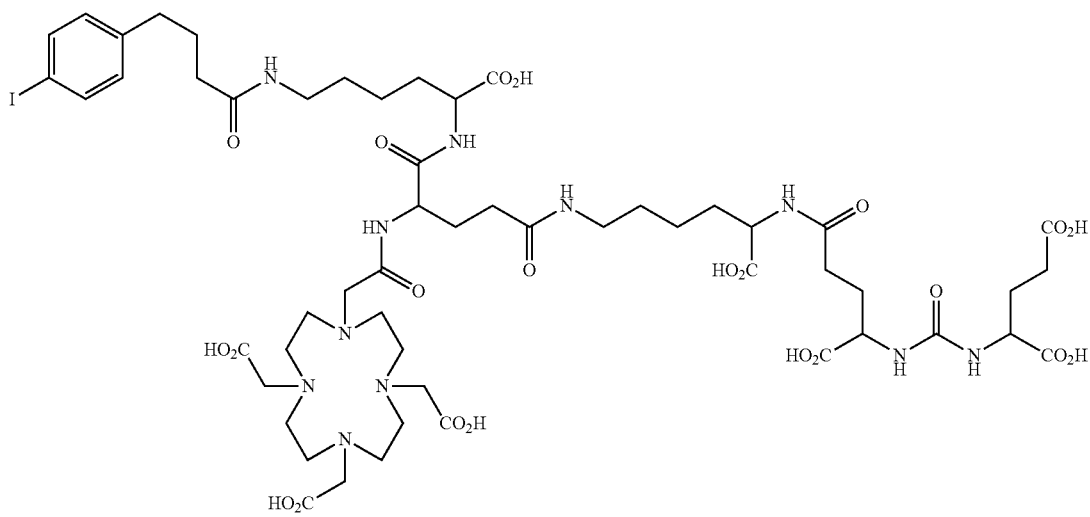 [SMILES: O=C(O)CCC(NC(=O)NC(CCC(=O)NC(CCCCNC(=O)CCC(NC(=O)CN1CCN(CC(=O)O)CCN(CC(=O)O)CCN(CC(=O)O)CC1)C(=O)NC(CCCCNC(=O)CCCc1ccc(I)cc1)C(=O)O)C(=O)O)C(=O)O)C(=O)O]

or a pharmaceutically acceptable salt thereof.

17. A pharmaceutical composition comprising a compound of claim 1 and a pharmaceutically acceptable carrier.

18. A method for imaging one or more prostate cancer cells in a patient comprising administering to the patient a compound of claim 1 and imaging the patient with positron emission tomography.

19. A compound of Formula (I)

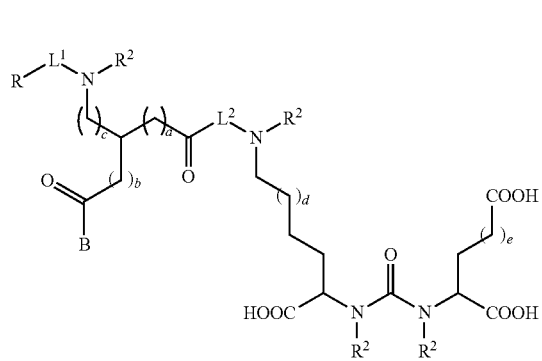

or a pharmaceutically acceptable salt thereof, wherein $L^1$ is a covalent bond or a divalent linking group;

$L^2$ is a divalent linking group;

R is a chelating agent optionally chelating a therapeutic radioisotope or a PET-active, SPECT-active, or MRI-active radioisotope, or R is a therapeutic drug;

B is a group of the formula:

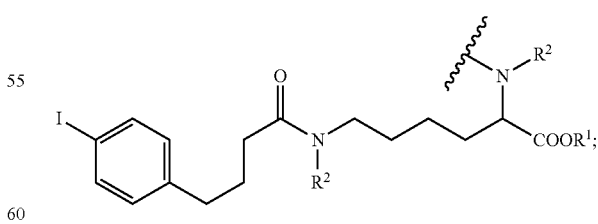

each a, b and c is independently 0, 1, 2 or 3;

d and e are each independently 0, 1, 2, 3, 4 or 5;

$R^1$ is hydrogen, $C_1$-$C_6$ alkyl or a protecting group; and each $R^2$ is independently hydrogen, $C_1$-$C_6$ alkyl or a protecting group.

20. A compound of Formula (I)

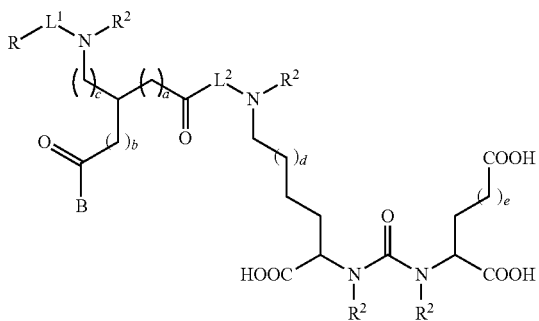

or a pharmaceutically acceptable salt thereof, wherein $L^1$ and $L^2$ are each independently a covalent bond or a divalent linking group;

R is a chelating agent optionally chelating a therapeutic radioisotope or a PET-active, SPECT-active, or MRI-active radioisotope, or R is a therapeutic drug;

B is a group of the formula

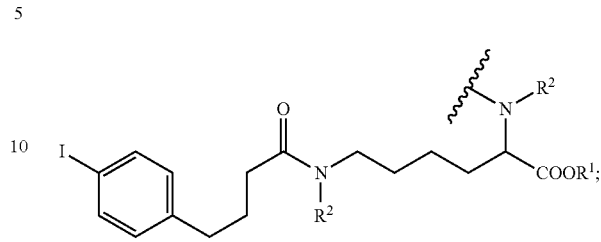

a is 1, 2 or 3; and
each b and c is independently 0, 1, 2 or 3;
d and e are each independently 0, 1, 2, 3, 4 or 5;
$R^1$ is hydrogen, $C_1$-$C_6$ alkyl or a protecting group; and
each $R^2$ is independently hydrogen, $C_1$-$C_6$ alkyl or a protecting group.

* * * * *